US010025908B1

(12) United States Patent
Orellano et al.

(10) Patent No.: US 10,025,908 B1
(45) Date of Patent: Jul. 17, 2018

(54) MEDICATION ADHERENCE SYSTEMS AND METHODS

(71) Applicants: Leonardo Y. Orellano, Tampa, FL (US); Gina L. Orellano, Tampa, FL (US)

(72) Inventors: Leonardo Y. Orellano, Tampa, FL (US); Gina L. Orellano, Tampa, FL (US)

( * ) Notice: Subject to any disclaimer, the term of this patent is extended or adjusted under 35 U.S.C. 154(b) by 15 days.

(21) Appl. No.: 15/050,184

(22) Filed: Feb. 22, 2016

Related U.S. Application Data

(60) Provisional application No. 62/120,784, filed on Feb. 25, 2015, provisional application No. 62/150,253, filed on Apr. 20, 2015.

(51) Int. Cl.
  *G06F 19/00* (2018.01)
  *G05B 15/02* (2006.01)

(52) U.S. Cl.
  CPC ......... *G06F 19/3462* (2013.01); *G05B 15/02* (2013.01)

(58) Field of Classification Search
  CPC .......................... G07F 11/62; G07F 17/0092
  See application file for complete search history.

(56) References Cited

U.S. PATENT DOCUMENTS

| 5,143,193 A * | 9/1992 | Geraci ..................... G07F 7/069 194/212 |
| 5,502,944 A * | 4/1996 | Kraft .................. G06F 19/3462 221/2 |
| 6,006,946 A * | 12/1999 | Williams ................ B65G 1/045 221/2 |
| 2004/0046020 A1* | 3/2004 | Andreasson .............. A61J 1/14 235/385 |
| 2004/0104652 A1* | 6/2004 | Holmes .................. A47B 88/00 312/348.3 |
| 2005/0060063 A1* | 3/2005 | Reichelt .................... G07F 5/18 700/244 |
| 2006/0058724 A1* | 3/2006 | Handfield ............. A61J 7/0084 604/20 |
| 2006/0136095 A1* | 6/2006 | Rob .......................... A61J 1/20 700/245 |
| 2006/0259195 A1* | 11/2006 | Eliuk ........................ A61J 1/20 700/245 |

(Continued)

*Primary Examiner* — Timothy R Waggoner
*Assistant Examiner* — Stephen L Akridge
(74) *Attorney, Agent, or Firm* — Stephen E. Zweig

(57) ABSTRACT

Automated medication dispensing system and device, designed to monitor and verify that a patient is being properly medicated. A sensor equipped, processor controlled, medication dispensing device is configured to store a plurality of medication doses, along with medication dispensing information, and to use its processor controlled actuators to automatically dispense this medication at the proper time when the sensors verify the patient's identity. The system also uses various combinations of built in and/or patient worn sensors to obtain evidence of proper medication. This evidence can include evidence that the patient has taken the drug, and/or evidence that the patient is physically behaving in a properly or improperly medicated manner. The system can be restocked with medication, often packaged in multi-dose cassettes, when medication runs low, and can also be configured using either an onboard user interface or a remote (e.g. Internet or local wireless) computerized device.

16 Claims, 18 Drawing Sheets

(56) References Cited

U.S. PATENT DOCUMENTS

| | | | | |
|---|---|---|---|---|
| 2007/0187423 | A1* | 8/2007 | Bedore | G07F 11/56 221/123 |
| 2008/0264967 | A1* | 10/2008 | Schifman | G07F 11/44 221/133 |
| 2008/0283542 | A1* | 11/2008 | Lanka | G06F 19/3462 221/6 |
| 2011/0313567 | A1* | 12/2011 | Willemse | G07F 9/026 700/242 |
| 2013/0172691 | A1* | 7/2013 | Tran | A61B 8/488 600/301 |
| 2013/0253700 | A1* | 9/2013 | Carson | G07F 9/006 700/236 |
| 2014/0361076 | A1* | 12/2014 | Iantorno | G06F 19/3462 235/381 |
| 2015/0203297 | A1* | 7/2015 | Manning | F25D 13/06 700/218 |
| 2016/0357940 | A1* | 12/2016 | Carter | A61J 7/0076 |
| 2017/0300659 | A1* | 10/2017 | Ziv | G06F 19/326 |
| 2017/0326033 | A1* | 11/2017 | Kraft | A61J 7/0084 |

* cited by examiner

MEDICATION ADHERENCE SYSTEMS AND METHODS

CROSS-REFERENCE TO RELATED APPLICATIONS

This application claims the priority benefit of U.S. provisional patent application 62/120,784, "MEDICATION ADHERENCE SYSTEMS AND METHODS", inventor Leonardo Orellano, filed Feb. 25, 2015; this application also claims the priority benefit of U.S. provisional patent application 62/150,253, "FALL DETECTION SYSTEMS AND METHODS", inventor Leonardo Orellano, filed Apr. 20, 2015; the contents of both of these applications are incorporated herein by reference.

BACKGROUND OF THE INVENTION

The present invention relates to medication adherence and automated drug administration systems in general, and more particularly, systems and methods to provide improved automated drug administration systems that also promote medication adherence.

The issue of medication adherence is a well-known problem in the field of health care. Positive patient outcomes from treatment require that therapies are delivered or performed as prescribed. However in the course of medical treatment, patients may be prescribed medication, treatments, or other therapeutic regimens which are administered on an outpatient basis, where the patient may not be directly observable by a health care practitioner. Although often, when a medical procedure, treatment, or therapy is performed on an outpatient basis, the procedure or treatment may be self-administered by the patient, not all patients are competent or reliable, and here medication compliance is an issue.

Although in some cases, family, friends, or designated caregivers may assist in delivery of outpatient medical care, in many situations obtaining the reliable assistance of a capable, willing, and responsible human caregiver may be problematic or prohibitively expensive. Thus in many situations such as home, outpatient clinic, nursing home, or other outpatient situations, there is a need to independently verify that the patient has followed the therapeutic regimen as prescribed. The need to independently verify patient compliance with a prescribed therapeutic regimen is often described in the art as "medication adherence" or "medical adherence". Various prior art drug administration systems have been proposed which use a variety of technologies and methods to promote and verify patient medication adherence.

Techniques used by some prior art systems to dispense medicine may include ejecting containers containing a single dose of medication. These prior art medical dispensing containers are frequently configured to permit dispensing of only a single medication, or multiple medications, in a sequential manner.

BRIEF SUMMARY OF INVENTION

In some embodiments, the invention may be a system of method of operating an automated medication dispensing device. This device may often be located in the patient's home or residence. The automated medication dispensing device will typically be configured to store a plurality of different medications in a plurality of individual compartments, each compartment storing a unit dose of at least one medication. This device will often be a processor (e.g. microprocessor, computer) controlled device, and will often also comprise other electronic components such as at least one communications interface (e.g. internet interface, wireless interface, and the like), onboard sensors, and the like. The medication device will mechanically dispense medication by using at least one processor controlled electronic actuator to retrieve medication from storage and provide this medication to a patient (or patient's caretaker).

The automated medication dispensing device will typically automatically dispense at least one medication by using its one processor controlled actuator(s) to either automatically retrieve the medication (or medications) from an appropriate compartment, or to automatically retrieve the appropriate compartment (containing this at least one medication) itself. The device will then use its actuator(s) to automatically deliver either the appropriate medication(s) or the compartment to the patient. Alternatively the device may deliver the mediation to the patient's caregiver, but as will be discussed, in a preferred embodiment, the recipient of the medication will often be the patient.

In a preferred embodiment, the device's processor(s) will be configured using both medication dispensing information (e.g. which medications to deliver at what days and times, as well as to which particular patient). Here this information is termed medication timing information and medication patient assignment information. The device will then often use at least one onboard sensor (which can be a short range wireless interface), and information pertaining to how the patient's identity correlates to sensor input (here termed reference patient identity information) to determine the patient's identity.

In a preferred embodiment, the device will then use this patient identity information, medication dispensing information, and time information (e.g. time and/or date as obtained from an internal or external clock) to automatically dispense at least one medication for the patient. The device can optionally be configured to handle more than one patient, and to distinguish between patients when dispensing medication.

In a preferred embodiment, typically after dispensing the medication(s), the device will then use the device's onboard sensors, and/or information obtained from various types of remote patient worn sensors, to obtain evidence that the patient(s) is being properly medicated. This evidence can include evidence that the patient has or has not taken the medication, and/or evidence that the medication is or is not working as expected. The device will receive this information, and typically at least store (e.g. in internal memory) or transmit (e.g. to a caregiver, healthcare professional, or other monitoring person or system) record(s) pertaining to this evidence.

DETAILED DESCRIPTION OF THE INVENTION

Figure 1:
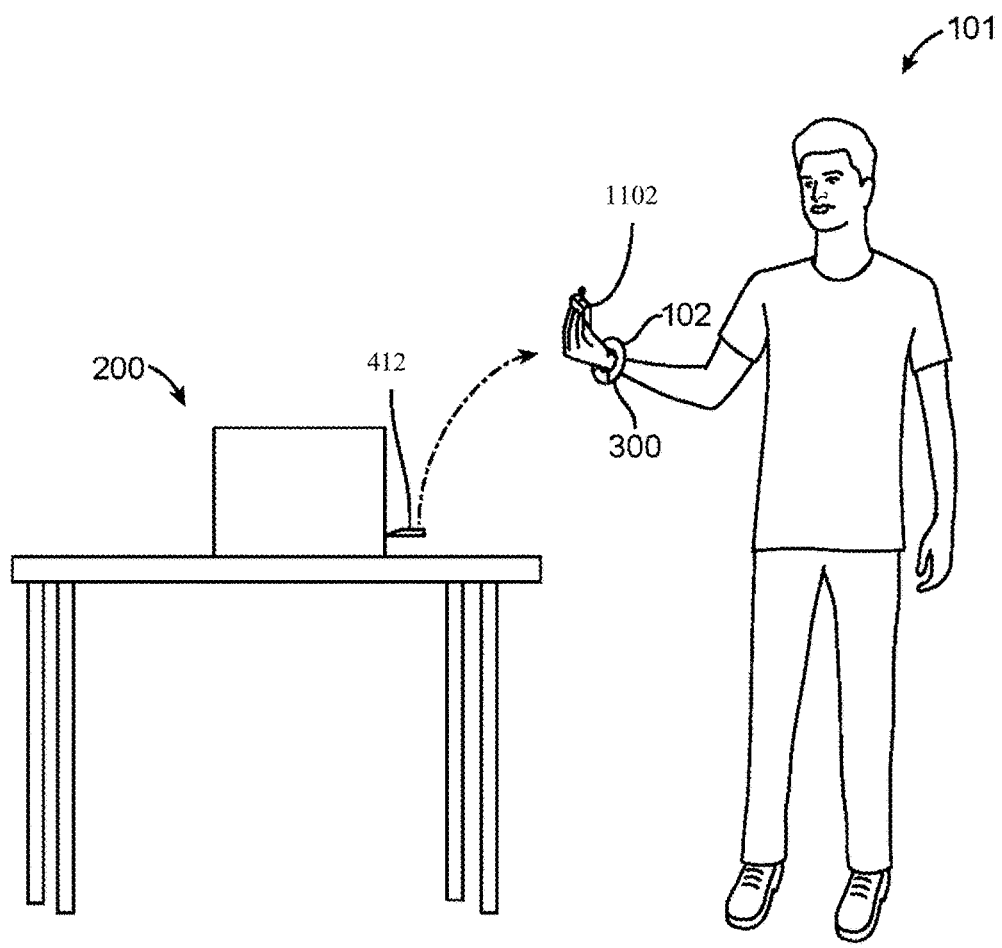
FIG. 1 illustrates a medication dispensing device and arm-band worn sensors in use by a patient, in accordance with an embodiment of the present invention.

As previously discussed, one major deficiency of prior art medication adherence/dispensing systems is that according to prior art, medication doses cannot always be easily adjusted, particularly by remote caregivers or healthcare professionals. Further it is difficult to simultaneously handle multiple patients with different dosing regimens. It is also difficult to make temporary modifications to a patient's medication regimen.

For example, a patient with a chronic, permanent, or semi-permanent condition may need certain therapeutic medications for that condition on a long-term or permanent schedule in a customized dosing regimen. However, the patient may also acquire a short-term condition such as cold or indigestion. Medical practitioners may also prescribe short-term therapeutic medications, however the existing medication adherence systems do not easily accommodate short-term adjustments to a medication regimen.

In addition, some medicines for short-term conditions may adversely interact with medication for chronic conditions, for example an anti-depressant improperly administered in combination with a decongestant may have serious side effects.

Existing medication adherence systems are typically capable of either dispensing one medication in sequence according to a defined schedule, or of dispensing multiple medications in sequence, according to a defined schedule. However existing medical adherence systems typically do not accommodate multiple medications delivered either to multiple patients, or to the same patient with different medical needs at different times. This is because the medicine dispensing apparatus in existing medication adherence systems are typically configured with medicine containers organized to operate in a sequential order, either first-in, first-out, first-in, last-out, or a related ordering, depending on the construction of the device. Such prior art systems do not give medical practitioners the opportunity to fine-tune, optimize, or adjust a patient's medication regimen to provide short term medications such as for a cold in combination with medications for chronic conditions such as for Alzheimer's disease.

For example, it might be medically desirable to prescribe a certain decongestant or sedative a certain number of hours after a dose of a certain Alzheimer's medication, after which time the patient's body may have metabolized the Alzheimer's medication to the point that levels in the patient's bloodstream are low enough so as to reduce the probability of adverse drug interaction to an acceptable level.

As part of the same example, consider another scenario for providing short-term adjustments to a treatment regimen to avoid adverse drug interaction. In some cases, it may also be desirable to further adjust near-term future doses of the Alzheimer's medication to permit regular dosing with the decongestant or sedative, until the decongestant or sedative is no longer needed. Once the decongestant or sedative is no longer needed, it would be useful to then return the previous dosing schedule for the Alzheimer's medication.

One problem here, however, is that prior art medication dispensing and control systems generally lack the ability to fine tune and adjust drug dispensing regimens in response to short term patient needs. This is a serious problem, which deny effective treatment for patients, as well as adverse drug interactions (e.g. if the timing of doses of different medications with adverse interaction potential cannot be adjusted to account for a patient's metabolic activity). In view of the deficiencies of the prior art in this area, there is a need in the field of medication adherence for improved medication dispensing and verification systems and methods.

Patient Identification Methods:

A medication dispensing and medication adherence system can also benefit if the system employs automated methods to confirm the identity of the patients that use the system. Here various types of individual identification methods known in the art may be used.

Techniques used to confirm patient identity can include speaker (e.g. voice) identification, patient face identification, and similar biometric techniques (e.g. fingerprints and the like). Further, in some embodiments, voice identification and face identification may be combined such that the probability of incorrectly identifying the patient, which otherwise might be too high if only one technique alone is used, may be reduced by use of multiple techniques.

Both facial recognition and voice recognition identification methods have issues, however. Facial recognition systems often require a training or configuration step wherein a system is provided with an example image to recognize. If a patient's appearance changes from the sample captured during the training step (for example due to injury, surgery, or similar short-term conditions), facial identification may fail. Another problem with facial recognition methods is that reliable face identification may require, in both training and testing modes, a compliant subject willing to present and physically orient their face in an optimal way. Not all patients are cooperative however. Some patients may be either unwilling or unable to comply with such constraints. Here, for example a drug rehabilitation patient or Alzheimer's may be unwilling to cooperate or comply.

Another problem is that automated facial identification techniques typically rely on well-known machine vision techniques and algorithms. These in turn often require adequate lighting, and under low light conditions, facial identification can fail. Unfortunately, patients often may be in low light conditions for a variety of reasons. Some patients may be light sensitive, and may have intentionally turned off the lights. Other patients may wish to trick the medication adherence system, and, again, intentionally turn off the lights. Other patients might have maintenance problems in their residence, or medication adherence may be needed during a power outage, such that adequate lighting is temporarily unavailable. Still other patients may be in low light conditions because they may be blind, and do not have need for lights, thus never turning the light on.

Voice identification methods have their own issues. Automated speaker voice identification methods may also fail due to the presence of noise (e.g. from household activity, whether from other residents or external causes). Voice identification based on automated audio processing may also fail if the subject does not cooperate with the identification procedure, or cannot provide a voice sample similar enough in the testing step to what was provided in the training step.

Machine voice identification methods also typically require a configuration or training step to configure the system with the parameters of the voice sample to be identified. Such machine speaker identification may also fail if the speaker's voice changes (for example due to injury, failure to wear false teeth during both training and testing, or due to illness such as a sore throat).

Thus although automated facial identification and voice identification methods can be useful, these methods can still fail to identify the patient in low light conditions, conditions with audible noise, or other situations which impair the performance of machine vision or speaker (voice) identification algorithms. Thus the need for improved methods of patient identification remains.

In addition to automated methods of identifying the patient, other issues related to automated medication adherence and dispensing techniques include automated methods of providing feedback regarding if the patient actually took the medication. Here machine vision methods, or machine sound (audio) analysis methods, may also be used to determine if the patient actually took the medication. For example, machine vision and machine audio processing may be used to identify the medication (e.g. by image processing), as well as to identify the patient physical activity or motion (e.g. the arm and mouth motion associated with swallowing a pill) associated with taking the medication. This information can then be used to confirm both that the correct medicine was dispensed, as well as to confirm that the patient's activity or motion is consistent with the patient actually taking the medicine as prescribed.

In this disclosure, the act of confirming (here in an automated sense unless otherwise specified) that a patient has consumed a medication may be interchangeably referred to as [automated]"dose compliance", or [automated] "drug adherence".

Automated medication adherence encompasses automated dose compliance and/or automated drug adherence. For example, computer based image processing algorithms can confirm whether a medicine tablet or capsule is the correct size, color, or shape, according to the characteristics of the prescribed medication. Machine vision and audio analysis of patient activity and motion may include the use of video object tracking to confirm, to at least some limited level of confidence, that the patient moved their hand, into which hand the medicine tablet or capsule was dispensed, to their mouth. These systems can also confirm, for example, that the patient then raised their hand holding a glass of water to their mouth.

Automated medication adherence systems may further confirm, to at least some level of confidence, that a given patient has taken a given medication by using machine audio processing to analyze and identify the sounds of swallowing, and/or using machine vision processing to identify the motion in the patient's throat caused by swallowing.

Other automated techniques may also be used by medication adherence systems to confirm, to at least some limited level of confidence, that a medication has been taken. Such alternative methods include weighing the medicine dispenser before and after a dose (where the weight should be less by the weight of one dose after successful dispensing), and other methods.

Although the present invention may, in some embodiments, use these above methods, in at least some embodiments, alternative methods, described below, may also be used. Here the objective is to provide for more flexible medication dispensing, more robust and flexible patient identification, and more effective confirmation of the patient's consumption of medication.

The present invention is based, in part, on an improved automated medication dispenser configured to provide automated random-access to medication. This improved medication dispenser can dispense a wide variety of different medications (often pill or other unit dose based) at any time, to allow short-term therapeutic doses on an as-needed basis.

The present invention is also based, in part, on an improved automated system that provides more robust patient identification. In some embodiments, this can be done by encoding automated patient identification functionality in a semi-permanent radio-frequency operative (RFID) tag or similar device (e.g. smart watch such as the Apple iWatch, and the like). Patient identification devices may also be packaged with other patient worn sensors, worn around the patient's neck, affixed elsewhere on the patient, or even implanted in a patient's body. Such patient identification devices can overcome problems of low light conditions, changed patient appearance, background noise, and other sources of error affecting machine vision, video, and audio analysis.

The present invention is also based, in part, on providing an enhanced automated identification of a patient's activity upon receiving a given medication from an automated medication dispenser. This can include automated methods of tracking the patient's motion using motion data obtained by various sensors. These sensors can include sensors such as gyroscopes, accelerometers, altimeters, magnetometers and other types of motion and position detectors, which may in some embodiments be worn by the patient (for example as various smartwatch motion and position sensors). Information from these sensors can be used to track and analyze, for example, the path of the patient's hand during a dosing action to help confirm whether a given medicine has been consumed.

In some embodiments, the present invention may be a combination of the various methods and systems described above. Such embodiments can be, for example, an intelligent (e.g. processor equipped) automated medication dispenser configured work in conjunction with wireless data obtained from one or more patient worn sensors, as well as various programs and algorithms designed to help insure that the patient is properly receiving appropriate mediation. Here this automated medication dispenser may occasionally be referred to in the alternative as a "medication dispensing device".

In some embodiments, the invention's "medication dispensing device" can comprise the above automated medication dispenser, as well as other components such as one or more embedded processor(s), optional video camera, optional time-of-flight camera, optional machine vision algorithms, optional machine audio processing algorithms, optional user interfaces, optional communication links, and the like.

Various types of automated medication dispensers may be used. This disclosure will focus on one particular example, but this particular example is not intended to be limiting.

One example of an automated medication dispenser disclosed herein, which can be used for some embodiments of the invention, employs a plurality of linear cassettes distributed around the center of a rotating robotic arm in roughly a cylindrical (or portion of a cylindrical) manner. This rotating robotic arm pivots (under processor control) around an adjustable height center joint, where the adjustable height center joint can raise or lower, as a result of processor commands, the height of the robotic arm.

Each cassette can store a plurality of refillable medicine bins at various heights (locations, positions) along the cassette. Each medicine bin will typically contain at least one dose of medication (e.g. one or more pills) for a particular patient. The rotating robotic arm, which operates under processor control, can be commended select a particular medicine bin by rotating to the cassette where that medicine bin is located, elevate to the correct height of the particular medicine bin, grab and remove a particular medicine bin from that cassette. The rotating robotic arm can then deposit that particular medicine bin (or the drug contents of the medicine bin) in an exit chute or channel, where the medicine bin (or the drugs themselves) can then be retrieved, the dose of medication removed, and subsequently taken by a patient.

In practice this automated medication dispenser can be alternatively viewed as being a type of rotating medicine dispensing rack. The robotic arm operates according to various stepper motors (a specific type of processor controlled actuator), and lead screws or other gearing mechanism. Medication may be dispensed by the medication dispensing device by using these stepper motors and leadscrews to direct the rotating robotic arm to operate re-fillable medicine bins loaded into the dispensing rack. In some embodiments, the various Medicine bins may be equipped with magnetic encoders or other type of identification (e.g. optical encoders, optical bar coders, optical bar codes) for sensing and identification by the medication dispensing device's control system software.

In some embodiments, the medication dispensing device control system software can further comprise custom application software and drivers running under an embedded operating system (e.g. Linux, Windows, iOS, Android, or other) to operate the robotic arms' various lead-screws and stepper motors (actuator), and to sense optical or magnetic encoder (or other device internal status) inputs from the dispensing rack to dispense medication.

The medication dispensing device control system software can also include custom application and driver software configured to interact with a human user or patient through various types of user interfaces, for control, training, authentication, and medication adherence purposes. In some embodiments the medication dispensing device can further comprise various types of wired, optical, or wireless communication interfaces/links such as any of WiFi, Ethernet, GSM, BLE, Zigbee, NFC, RFID, or other communications links. Data sent over these links can be used for various purposes including command, control, reporting, configuration, authentication, sensing, and other purposes. The medication dispensing device may use these various types of communication links to communicate with other devices locally or via an Intranet, VPN, Internet, ad-hoc network, or other network topology.

In some embodiments, the invention may further use data obtained from patient worn sensors such as data obtained (often by wireless transmission) from arm-worn sensors (e.g. Apple iWatch type devices, custom arm-band devices, and the like) to monitor patient medication compliance.

Various types of patient-worn sensors and devices can be used to help monitor patient compliance. In some embodiments, the patient worn devices can provide data (again typically by wireless methods such as WiFi or Bluetooth™ connections) such as patient identification data, motion sensor data, position sensor data, GPS sensor data, GSM sensor data, and the like.

In addition to working with patient worn sensors, the medication dispensing device can additionally employ data obtained from other types of built in sensors or other local sensors, such as cameras, microphones, audio output devices, audio input devices, switches, smartphones, tablets, and other devices or systems.

Although the automated medication dispenser will normally have its own onboard processor(s), it is not an absolute requirement that every aspect of the medication dispensing device be controlled by the processors onboard the automated medication dispenser. In some embodiments, at least some of the processors and algorithms used for patient medication compliance and to monitor and control the automated medication dispenser may be located on various types of remote devices. These may be local remote devices (e.g. local computerized devices) or even remote internet servers. However in at least some embodiments of the invention, at least some and occasionally often all of the various mediation dispensing device automated functions

Patient Movement Monitoring

A patient who is immobile, or a patient who exhibits unusual patterns of motion about a residence, may both represent a patient who is either not in compliance with the patient's medication, or alternatively the existing medication may be ineffective. Thus in some embodiments, the medication dispensing device may optionally use one or more communication links (often wireless links) to receive information pertaining to patient movement from room to room in a dwelling. For example, patient movement status information can be obtained from various types of door position switches or motion sensors, and thus detect and report on patient movement about the patient's residence, or outside of the patient's dwelling. Alternatively the system may sense the patient's position through use of various patient worn sensors, such as patient worn GPS sensors, WiFi sensors, or even alternative methods such as determining if a short-range wireless signal emitted by a device worn by the patient can be detected.

Thus for example, if the medication dispensing device control system software detects that a patient has skipped their medication, and is also exhibiting unusual patterns of mobility (e.g. wanders outside of a safe area), the medication dispensing device's control system software may automatically alert health care workers, caregivers, family members, or authorities.

Such alerts may be done by various means, including automated phone calls, emails, alarms, text or SMS messages and the like. Additionally the medication dispensing device system may record the information for auditing purposes, or take other actions as configured.

Exchanging Information with Healthcare Professionals and Healthcare Institutions:

In some embodiments, the medication dispensing device may also be configured equipped to seamlessly exchange information (which can include patient and/or medication data) with hospitals, pharmacies, physicians, and other medical organizations or providers. Here use of standard medical communications and data interchange protocols, such as the HL7 hospital protocol, may be useful.

User Interfaces:

In some embodiments, the automated medication dispenser portion of the medication dispensing device may further implement a mediation dispensing device user interface. This user interface can, for example, include various devices such as one or more LCD displays with touchscreen input, one or more audio speakers, microphone(s), wireless scanners and the like which form part of the automated medication dispenser itself. In other embodiments, the automated medication dispenser may be configured to alternatively provide web browser pages or work with apps, such as smartphone apps, to enable the user interface to be provided by external computerized devices. In other embodiments, the medication dispensing device user interface may be provided by a computerized device external to the automated medication dispenser, such as a remote internet server. Here, however, we will focus on the case where the automated medical dispenser itself provides the user interface by way of at least one built in touchscreen user interface, and also audio and video sensors, as a particular example.

In some embodiments, the automated mediation dispenser itself may also provide, either directly (e.g. by direct Bluetooth connectivity) or through a router such as a WiFi router, communications links (e.g. wireless connectivity) to sensors and/or patient identification data provided by a patient worn or implanted device such as an arm-band, smart watch, RFID (Radio Frequency Identification) tag, and the like.

In some embodiments, the user interface may be used by either on-site caregivers or higher-functioning patients to view patient or device status, make requests, or respond to requests for information from remote healthcare professionals or caregivers.

Focusing on the case where the automated medication dispenser provides the user interface and suitable interface devices, in some embodiments, the automated medication dispenser may have an audio speaker that can be used to provide voice prompts and commands to patients. This audio interface can be used, for example to notify the patient it is time to take a medication, to approach the medication dispensing device, to re-orient themselves in front of a built in automated medication dispenser camera to attempt machine vision authentication, or otherwise interact audibly with the patient or a caregiver.

In some embodiments, the automated medication dispenser may employ various drug removal sensors to determine if the dispensed medication or medication bins have been removed from an appropriate receptacle in a timely manner. These drug removal sensors can be, for example, weight sensors, photodetector or image sensors, vibration sensors, and the like. If, for example, the drug removal sensors detect that a dispensed dose of medication was removed from the receptacle in a timely manner, then this itself constitutes some evidence that the patient may have taken the medication. Similarly if the drug removal sensors detect that a dispensed dose of drug was not removed from the receptacle in a timely manner, then this would constitute at least some evidence that the patient has not properly taken the medication.

In embodiments where the automated mediation dispenser has a built in video camera, this video camera can serve multiple purposes, including patient authentication, verification of patient medication adherence, and other types of audits.

For example, in some situations, it may be desirable to configure the system so that the patient's identity (patient authentication) is automatically verified (e.g. by software facial recognition) before the automated medication dispenser dispenses medication. It may also be desirable to configure the system to attempt to automatically confirm (e.g. by automated vision methods) that the patient has actually taken the medication.

Video authentication of patient identity can be implemented by control software configured with one or more machine vision algorithms, in combination with video input from the camera, which often will be built into the automated medication dispenser. In addition to automated facial identification methods, other identification methods such gait identification, gender identification, height identification, or other visual authentication techniques may also be used.

Audio patient identity verification methods may also be used. Here control software configured with one or more machine audio processing and analysis algorithms, such as voice or speaker identification can be used, typically in combination with audio input from a microphone that is built into the automated medication dispenser.

In some embodiments, where the medication dispensing device can use a video camera and machine vision algorithms for motion tracking and gesture identification in order to that the patient is taking the medication properly Video support for confirming medication adherence can be implemented by configuring the device control software with one or more video image and motion interpretation analysis algorithms. These may include algorithms for video motion tracking, or patient gesture identification (e.g. tracking a motion of a hand to the patient's mouth) that use video signals (often from a video camera that is a part of the medication dispensing device) to confirm that after the device has output a given drug, the patient has then made the appropriate motions, activities, or other visual events consistent with consuming that medication dose.

Either additionally or independently from any video analysis, the medication dispensing device can also use a microphone (such as a built-in microphone) and suitable machine (e.g. software and processor based) audio processing and analysis algorithms to also confirm medication adherence. In these embodiments, audio support for medication adherence in the medication dispensing device can be implemented by control software configured to process and analyze audio input from one or more microphones using various types of audio processing or analysis algorithms. For example, these audio processing algorithms may comprise at least some automated voice recognition algorithms.

In these embodiments, the medication dispensing device/automated medication dispenser may first prompt the patient with an audio prompt (through a built-in speaker) or video prompt (thought a built in display screen) or other prompt to confirm that a given dose of medication was taken. The voice recognition algorithms can then listen to determine whether a patient answers "Yes", or "No". In some embodiments, the device may also employ sound recognition algorithms to detect and identify sounds associated with patient activity such as swallowing.

If further verification records are desired, the automated medication dispenser/medication dispensing device may also be configured to capture and record video of the patient using the medication dispensing device. Here this captured video can be periodically reviewed by caregivers to ensure the patient is using the medication adherence system correctly and receiving medication as prescribed.

Remote, Patient Worn, Sensors:

In some embodiments, evidence of proper patient medication may also be obtained by using various types of remote (i.e. not built into the medication dispensing device itself) patient worn sensors. These sensors may be positioned in various portions of the patient's body. In this discussion, we will focus on wrist or arm worn sensors, here called "patient worn sensors", however this particular location is not intended to be limiting.

Such remote patient worn sensors may be either device provided by third parties (e.g. smartwatches such as the Apple iWatch) that may be configured to work with the automated medication dispenser by suitable software uploads or "apps". Alternatively, the remote patient worn sensors may be custom built to work only with the automated medication dispenser.

In either case, the remote patient worn sensors will often have onboard memory, often have their own processors and software, and often also wireless transmitters or transceivers configured to at least transmit data to the automated medication sensor/medication dispensing device, either directly or via an intermediate step such as by a WiFi router.

In some embodiments, the remote patient worn sensors may be configured with patient identification data, and/or also equipped with various types of sensors such as motion tracking sensors and the like. These motion tracking sensors can, for example, comprise any of gyroscopes (e.g. electronic gyroscopes), accelerometers, altimeters, and magnetometers and the like, and in some embodiments even GPS (global positioning system) receivers to track gross changes in patient position/location. Often some of all of the above sensors and components may be part of a single patient worn device.

Typically the remote patient worn sensors will use communications links, often short-range wireless communications links such as WiFi or Bluetooth links, to transmit data pertaining to the patient's motion to the medication dispensing device for further analysis (typically automated analysis, although some data may also be manually reviewed as well as desired).

The automated medication dispenser/medication dispensing device can use data provided by the remote patient worn sensors to confirm proper patient medication according to various algorithms, including:

A: Confirming by patient motions (e.g. arm motions) that the patient has made arm gestures compatible with taking mediation at the appropriate time points.

B: Detecting instances of abnormal patient motion, such as situation where the patient falls down. This may be distinguished from normal instances of patients sitting down or laying on a bed because the acceleration may be more abrupt, and additionally the location in the dwelling may be an unusual location. Here, for example, such "fall detection" may be implemented in the medication dispensing device by control software configured with one or more algorithms for analysis of sensor data from the motion-tracking sensor in the arm-band, including gyroscope, accelerometer, altimeter, or magnetometer data. When this occurs, in addition to possible alerts being given to caregivers, the system can use this as evidence that the patient is not being properly medicated, either due to not adhering to schedules for taking medication, adverse drug interactions, or change in patient medical status potentially requiring an adjustment in medication or other medical intervention.

As previously discussed, in some embodiments of the present invention, the medication dispensing device may receive GPS coordinates from either the remote patient worn sensors or other patient worn devices, such as a patient's smartphone or other portable device. Note that in some embodiments, electronic devices normally carried by a patient, such as smartphones, may themselves be used as remote patient worn sensors. This is because modern smartphones, exemplified by the popular iPhone series, are themselves equipped with suitable motion sensors and communications capability, and such smartphones are often carried by patients throughout the day.

Such GPS functionality can be useful because GPS position information can be used to alert both the automated medication dispenser/medication dispensing device (as well as human caregivers) if the patient unexpectedly strays outside of a pre-configured area. This information may be particularly relevant as evidence of a possible medication problem if GPS reported patient unexpected locations can be correlated with missed medication doses, or abnormal times of day. Here, for example, a patient wandering outside of a house at 3 AM, in conjunction with evidence of a possible skipped dose of medication, could be sufficient to automatically cause the system to trigger an improper medication alarm which in turn might notify appropriate caregivers.

Here the main idea is that only one type of sensor data regarding evidence of proper patient medication might not by itself be grounds for automatically taking action, when the system detects multiple irregularities from multiple sensors, the reliability that the system can automatically detect that the patient is improperly medicated can increase. Thus the system can combine various sets of data, such as machine vision analysis of video for face identification, arm-band (e.g. patient worn) authentication method of confirming patient identity (e.g. patient worn RFID tags), remote patient worn sensors, and the like can:

A: Increase the level of confidence that the patient has been correctly identified before dispensing medication.

B: Increase the probability of connecting significant evidence as to if the patient is being properly medicated or not.

As previously discussed, in some embodiments, the present invention can use the motion-tracking sensor in the patient worn sensors or other patient worn sensor, in (usually wireless) communication with a medication dispensing device, to track and identify the motion of a patient's hand as the medicine is taken. Such taking medication is often accompanied by other related, follow-up actions, such as drinking a glass of water to complete a dosing procedure, and these related actions may also be monitored.

For example, the measurements provided by an patient arm worn motion-tracking sensor can enable the three dimensional path of the patient's hand to be traced as medication is dispensed and consumed, and this can be used as evidence of medication adherence. This mechanical motion method of monitoring medication adherence may be used, for example, to either supplement other sensor data, such as machine vision data, or as a fallback procedure available when machine vision techniques fail.

Machine vision techniques can fail in a variety of situations. These situations can include low light conditions, failed cameras, machine learning training errors (e.g. not trained yet), as well as situations where the patient's facial appearance or mechanical dosing motion changes suddenly or temporarily (e.g. due to injury, surgery, illness, the need to wear a therapeutic arm wrap). In other situations, machine vision techniques may fail to identify the visual characteristics of the patient's dosing motion. Thus in some embodiments, use of patient worn motion sensors to detect patient drug taking motions may be used in combination other sensor data, such as machine vision techniques, machine audio analysis, and the like. This can diminish patient privacy, however. Thus in other embodiments, data from patient worn motion sensors can be used directly without supplemental video or audio methods. These later embodiments, although potentially not quite as robust, do enhance patient privacy.

The mechanical motion method of ensuring medication adherence may also be effective in combination with a secure wireless authentication system comprising, in a non-limiting example, patient authentication data embedded in the patient's patient worn sensors or implanted in the patient's hand or arm, with the patient authentication data in the patient worn sensors presented to the medication dispensing device for authentication using an inter-operable scanning or reading device in the medication dispensing device.

The motion-tracking sensor can, for example, use one or more gyroscopes, accelerometers, altimeters, or magnetometers, to confirm the path traced by a patient's hand conforms to a path for a successful dose. In combination with machine vision analysis of video, the motion-tracking method for confirming medication adherence can increase the level of confidence that the patient consumed the medication. The altimeter is essential to determine the proximity to the patient's mouth. In some embodiments of the present invention, the medicine dispenser tray is a few inches from the surface the medicine dispensing device rests on, thus the point at which the medication is dispensed is known. The change in altimeter measurements from the beginning to the end of the patient's medicine-taking motion confirms the dose was moved high enough to be placed in the mouth. The altimeter may be equipped with a temperature sensor, to permit altimeter compensation for ambient temperature. A calibration step using machine vision techniques, which may include algorithms using Fisher Faces or Eigen Faces, may be used to identify the patient's facial features including the mouth, to confirm altimeter measurements for subsequent doses. In some embodiment of the present invention a remote control application can configure schedules and other parameters, and dispense medication. Further embodiments of the present invention may include add-ons to the medication dispensing device for measuring and reporting heart rate, blood pressure, temperature, and the like.

Although training steps are required for methods of authentication and medication adherence that rely on audio techniques such as voice identification, or imaging techniques such as gesture identification, gait identification, or face identification, the present invention can provide reliable medication adherence without training steps, through the use of the arm-band authentication technique in combination with the mechanical motion method of confirming the patient's compliance in taking the medicine. The only required input to the present invention, necessary to enable the present invention to provide reliable medication adherence without training the machine vision or machine audio algorithms, is the patient's height. The patient's height is used to determine an acceptable path, traced by the data from the mechanical motion sensor in the arm-band, of the patient's hand, as the patient consumes the medication. In combination with the machine vision analysis and machine audio analysis techniques known in the art, the new methods and systems disclosed herein for arm-band authentication and mechanical motion medical adherence provide improved levels of confidence and assurance that the patient has been correctly authenticated, in addition to increased confidence and assurance that the patient has consumed the medication as prescribed.

Further Discussion

As previously discussed, the automated medication dispensing device will typically be configured to store a plurality of different medications in a plurality of individual compartments, each compartment storing a unit dose of at least one medication. This device will often be a processor (e.g. microprocessor, computer) controlled device, and will often also comprise other electronic components such as at least one communications interface (e.g. internet interface, wireless interface, and the like), optional onboard sensors, and the like. The medication device will mechanically dispense medication by using at least one processor controlled electronic actuator to retrieve medication from storage and provide this medication to a patient (or patient's caretaker).

The automated medication dispensing device will typically automatically dispense at least one medication by using its one processor controlled actuator(s) to either automatically retrieve the medication (or medications) from an appropriate compartment, or to automatically retrieve the appropriate compartment (containing this at least one medication) itself. The device will then use its actuator(s) to automatically deliver either the appropriate medication(s) or the compartment to the patient. Alternatively the device may deliver the mediation to the patient's caregiver, but as will be discussed, in a preferred embodiment, the recipient of the medication will often be the patient.

In addition to patient identification and behavior sensors, the automated medication dispensing device will typically have other sensors configured to confirm correct operation. These can include internal sensors to confirm that the correct medication has been selected, internal sensors to check for abnormal operation (e.g. actuators operating incorrectly, medication not dispensed properly) and the like. Still other sensors can be used to confirm that the medication has been properly delivered to an appropriate drug dispensing location of the automated medication dispensing device, as well as detect when the medications have been removed from this location.

In a preferred embodiment, the device's processor(s) will be configured using both medication dispensing information (e.g. which medications to deliver at what days and times, as well as to which particular patient). Here this information is termed medication timing information and medication patient assignment information. The device will then often use at least one onboard sensor (which can be a short range wireless interface), and information pertaining to how the patient's identity correlates to sensor input (here termed reference patient identity information) to determine the patient's identity.

In some embodiments, the automated medication dispensing device can further comprise a user interface (e.g. a touchscreen and associated processor and software driven touchscreen user interface), and some or all of the medication dispensing information or reference patient identity information can be directly entered using this interface. Here, for example, a person might directly code in the medication schedule, patient ID, and the like). Alternatively the medication dispensing device might be connected, via its communications interface, to a remote computerized device (e.g. an internet connection to a remote computerized device) and medication dispensing information and/or patient identification might be entered in remotely. As yet another alternative, the medication dispensing device might have a local wireless connection (e.g. via WiFi, Bluetooth™) to local computerized devices (e.g. smartphones or other local computerized device), and the mediation dispensing information or reference patient identity information dispensed in that manner.

In some embodiments, the automated medication device's one or more optional onboard sensors may comprise any of video or time-of-flight or audio sensors. In these embodiments, the automated medication dispensing device's processor(s) can be configured to use automated video or time-of-flight or audio analysis software to confirm the patient's identity.

Indeed, in some embodiments, the automated medication dispensing device may also use its processor(s) and these optional onboard sensors, along with may automated video or audio or time of flight analysis software, to obtain evidence that the patient has also taken the most recently dispensed medication. Here evidence of moving a hand to the mouth, for example, or other characteristic medication taking motion or sound may be used, as previously discussed.

Alternatively, other methods of automatically verifying the patient's identity may be used. For example, in some embodiments, the patient may wear a radiofrequency identification tag (RFID tag) or other automatic identification device. In this case, the automated medication device's onboard sensors may comprise RFID tag sensors, or other automatic identification device sensors. In these embodiments the automated medication device' sensors can use this RFID tag ID data or other patient worn identification device data to automatically confirm the patient(s) identity.

In a preferred embodiment, the device will then use this patient identity information, medication dispensing information, and time information (e.g. time and/or date as obtained from an internal or external clock) to automatically dispense at least one medication for the patient. The device can optionally be configured to handle more than one patient, and to distinguish between patients when dispensing medication.

In a preferred embodiment, typically after dispensing the medication(s), the device will then use the device's onboard sensors, and/or information obtained from various types of remote patient worn sensors, to obtain evidence that the patient(s) is being properly medicated. This evidence can include evidence that the patient has or has not taken the medication, and/or as evidence that the medication is or is not working as expected. The device will receive this information, and typically at least store (e.g. in internal memory) or transmit (e.g. to a caregiver, healthcare professional, or other monitoring person or system) record(s) pertaining to this evidence.

In some embodiments, the medication device's processor may be configured to work with data obtained (often via a wireless link) from remote patient worn sensors. Often these remote patient worn sensors may be worn on the patients arm or wrist, but other locations on the patient may also be used. These remote sensors can, for example, comprise patient worn motion or position sensors, typically with wireless connectivity to the automated medication dispensing device. In these embodiments, the automated medication device's processor can be further configured to use the patient motion or position data obtained from these patient worn motion or position sensors to obtain evidence that said patient is being properly medicated.

Here, for example, evidence of suitable patient arm motions (e.g. patterns of acceleration and deceleration) characteristic of moving the hand to the mouth, at an appropriate time soon after medication has been dispensed, may be used as evidence that the patient has taken the medication.

Alternatively or additionally, the patient worn sensors can be motion or position or location sensors that further report on the motion, or position/location of the patient on a continuing basis. In these embodiments, the processor onboard the automated medication dispensing device can be further configure to use evidence of abnormal patient motion, or position/location as evidence that the patient has not been adequately medicated. Here, for example, this evidence can comprise evidence of patient falling, lack of motion, abnormal gait, tremors, or patient position outside of predetermined position or position and time limits (e.g. an improperly medicated patient is wandering around in circles outside the house at 3 AM).

In a preferred embodiment, at least when the automated medication device detects such evidence of improper medication, the automated medication device's processor can then use the device's communications interface to transmit this evidence to a remote computerized device (such as a caregiver or healthcare professional). The automated medication device will preferably also send other types of information, such as the status of the automated medication dispensing device (e.g. working OK, low on medication, malfunction, etc.) to remote computerized devices as well for various maintenance purposes.

In terms of the mechanical operation of the automated medication device, various embodiments are possible. Some of these are discussed below.

Figure 4:
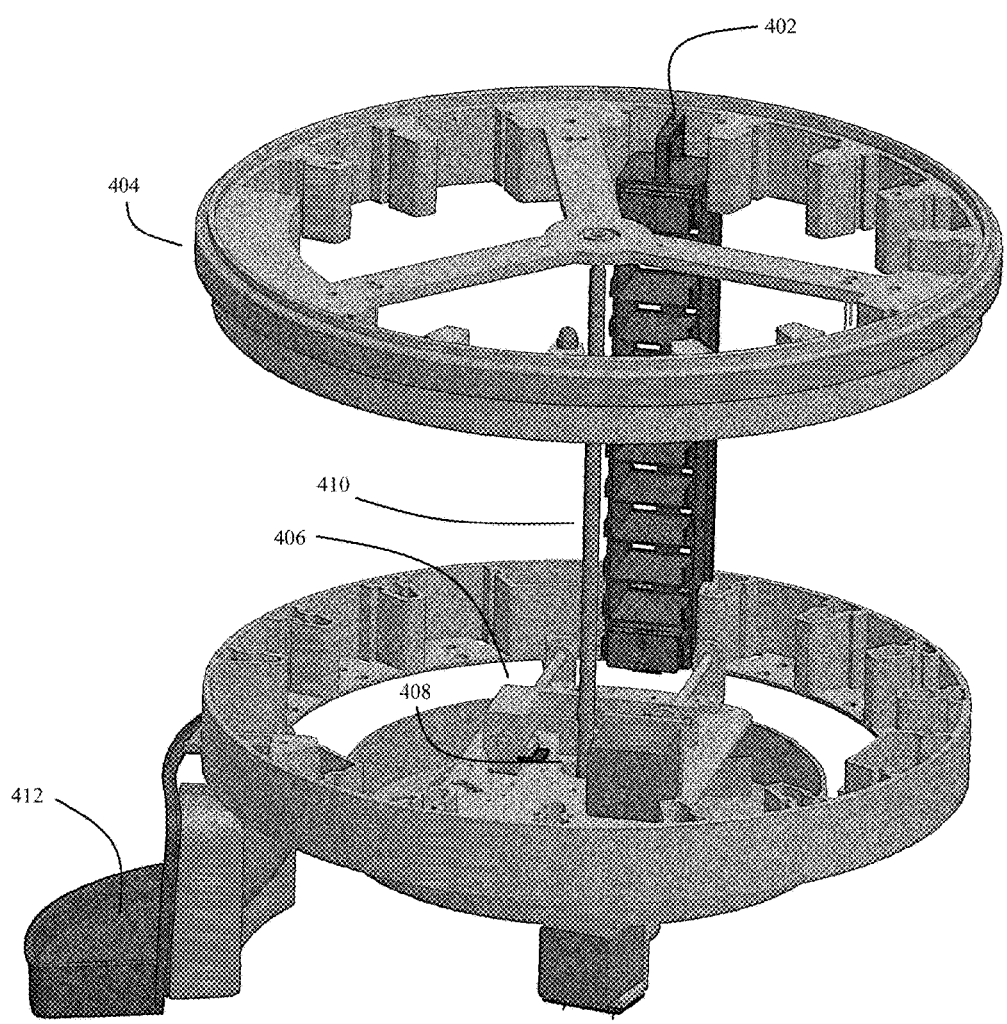
FIG. 4 illustrates shows one embodiment of the invention where the device has cassette slots disposed along the circumference of a cylinder, and one of these cassette slots is occupied by a linear cassette. This linear cassette has two medicine bins. The position of the robotic arm and the drug dispensing location is also shown. Note that the words "cassettes" and "cartridges" are used interchangeably in this disclosure.
Figure 10:
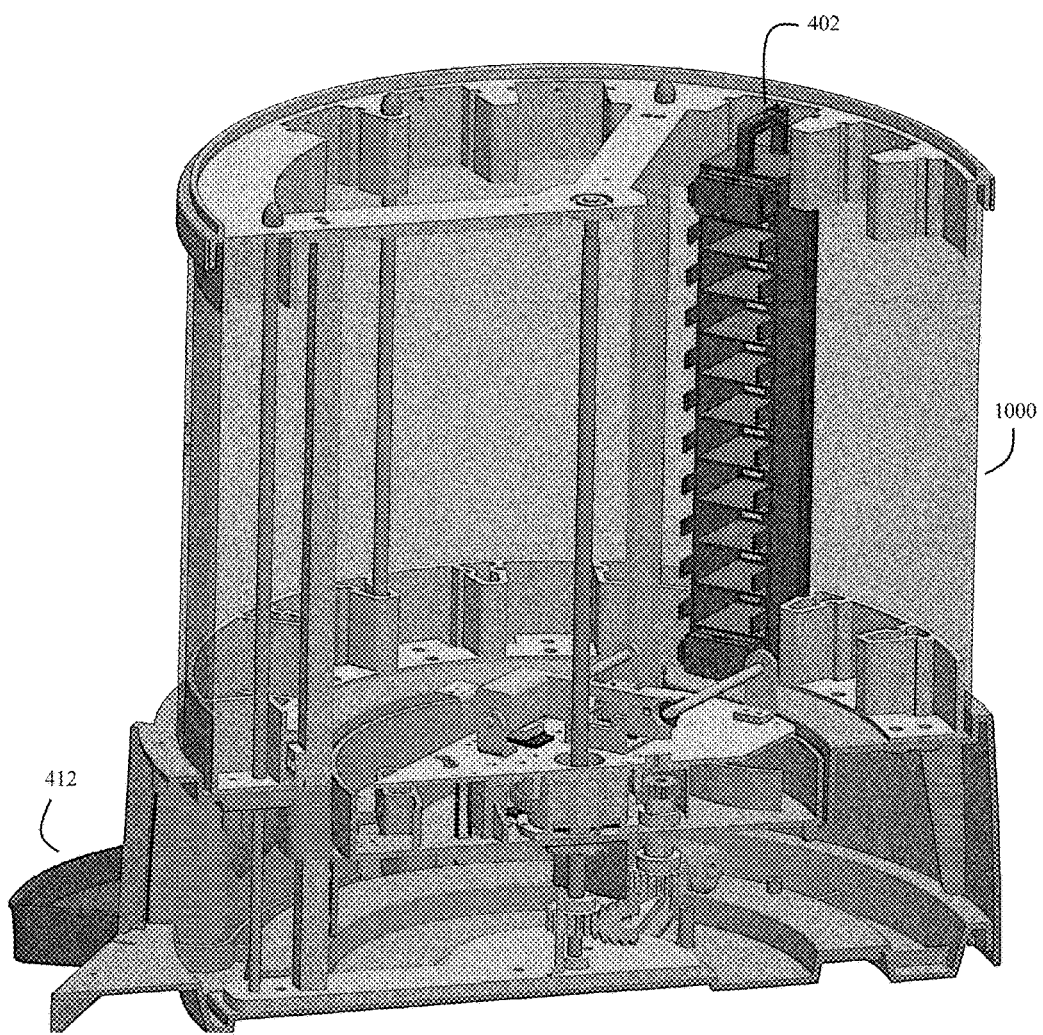
FIG. 10 shows a cross section of one embodiment of the automated medication dispensing device.
Figure 11:
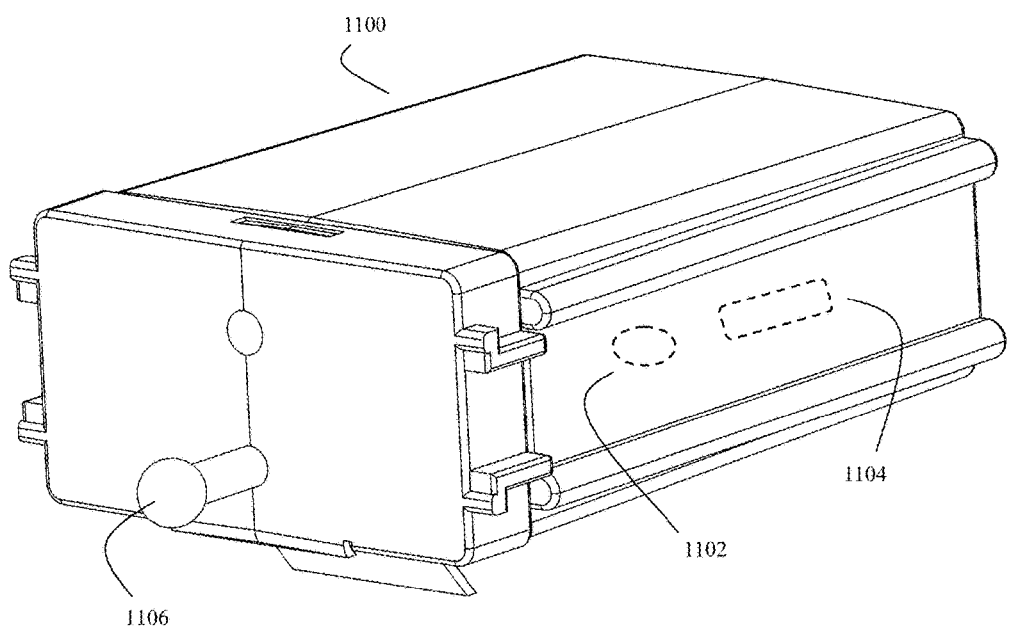
FIG. 11 illustrates a medicine bin, showing the position of two pills stored inside the bin. Note the protruding ball-like handle on the bin, which can be used to help interface with a gripper portion of a robotic arm.
Figure 12:
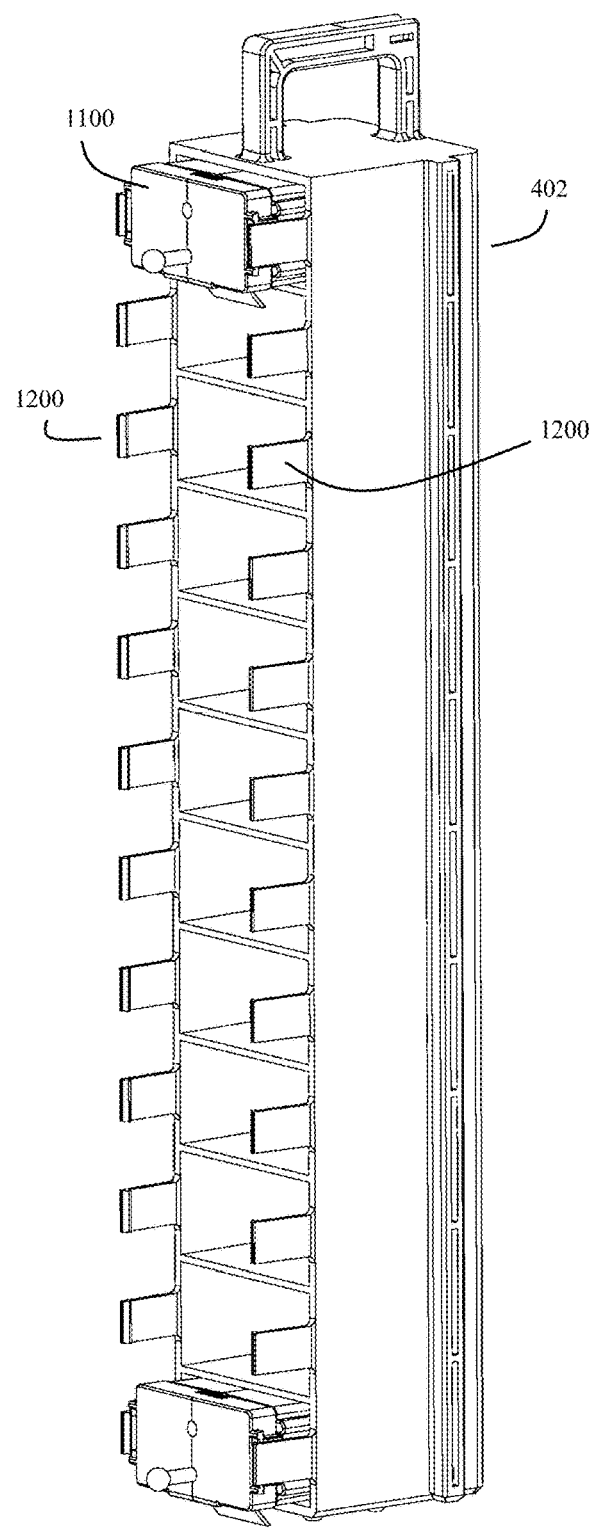
FIG. 12 shows a linear cassette, containing two medicine bins, and ten empty medicine bin slots.

FIG. 4 shows some of important components of one embodiment of the invention. Additional detail is also shown in FIG. 10, FIG. 11, FIG. 12, and other figures to follow.

In the embodiment shown in FIG. 4 and elsewhere, the plurality of individual compartments comprise a first plurality of removable linear cassettes (402), each removable linear cassette storing a second plurality of unit doses of at least one medication. This plurality of removable linear cassettes (402) can be disposed in a cylindrical or partial cylindrical circumference manner (404) around a robotic arm (406) that pivots around a center point (408) disposed along an axis of the cylinder (410). In some embodiments, these removable linear cassettes (402) can be positioned with their longest dimension parallel to this axis (410). In this embodiment, processor controlled actuators direct robotic arm (406) to rotate around this axis (410) to a processor designated linear cassette (402), as well as move along (here up and down) axis (410) to a specific level on the designated linear cassette (402) where a designated unit dose of at least one medication is located.

The processor can then retrieve the unit dose of the at least one medication and automatically dispense medication by depositing the unit dose of the at least one medication in a drug dispensing location (412) of said automated medication dispensing device.

Note that typically, these components will be behind a covering so that the patient will not be tempted to try to retrieve the medication directly. This covering is shown in more detail in FIG. 10A (1000)

In some embodiments, the automated medication dispensing device and the linear cassettes (402) are configured so that the automated medication dispensing device can be refilled by removing empty linear cassettes (402), and refilled by inserting medication filled linear cassettes.

As shown in more detail in FIGS. 11 and 12, in some embodiments, the plurality of individual compartments can comprise a second plurality of medicine bins (1100), each medicine bin configured to store a unit dose of at least one medication (here in FIG. 11, two different pills 1102 and 1104 are shown).

As shown in FIG. 12, this second plurality of medicine bins (1100) can be distributed into a first plurality of removable linear cassettes (402). Here each removable linear cassette (402) can store a second plurality of medicine bins (1100). In this example, linear cassette (402) has space for twelve medicine bins (1100), and of these twelve spaces, two are occupied with medicine bins (1100), and ten are empty. So this second plurality is twelve.

As FIG. 4 and other figures show, this embodiment of the device has openings to hold thirteen linear cassettes (402), so the first plurality in this example is thirteen. This first plurality of removable linear cassettes (402) disposed in a cylindrical or partial cylindrical circumference manner around a robotic arm (406) that pivots around a center point (408) disposed along an axis of the cylinder (410), and the removable linear cassettes can positioned with their longest dimension parallel to this axis (410).

In this embodiment, the processor controlled actuators can direct robotic arm (406) to rotate around axis (410) to a processor designated linear cassette (402), move along (e.g. up and down) axis (410) to a specific level or position on linear cassette (402) where a designated medicine bin (1100) is located, and retrieve either the designated medicine bin or a unit dose of at least one medication stored in the designated medicine bin. The system can then automatically dispense medication by depositing either the medicine bin (1100) or the unit dose of the at least one medication (e.g. 1102, 1104) stored in medicine bin (1100) in a drug dispensing location (412) of the automated medication dispensing device.

Figure 13A:
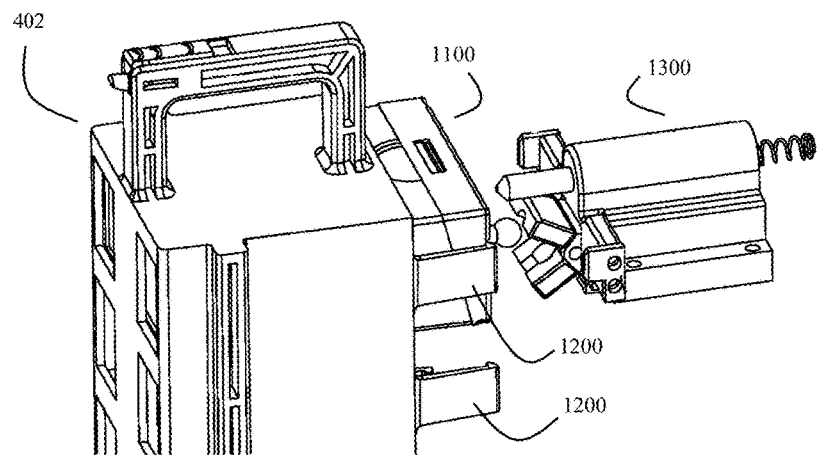
FIG. 13A illustrates a perspective view of a gripper of a robotic arm just before engaging with protruding handle to grab a medicine bin, in accordance with an embodiment of the present invention.

In FIG. 13A, an actuator controlled gripper (1300) located on robotic arm (406) (not shown) is shown about to grasp a handle or knob (1106) attached to medicine bin (1100).

Figure 13B:
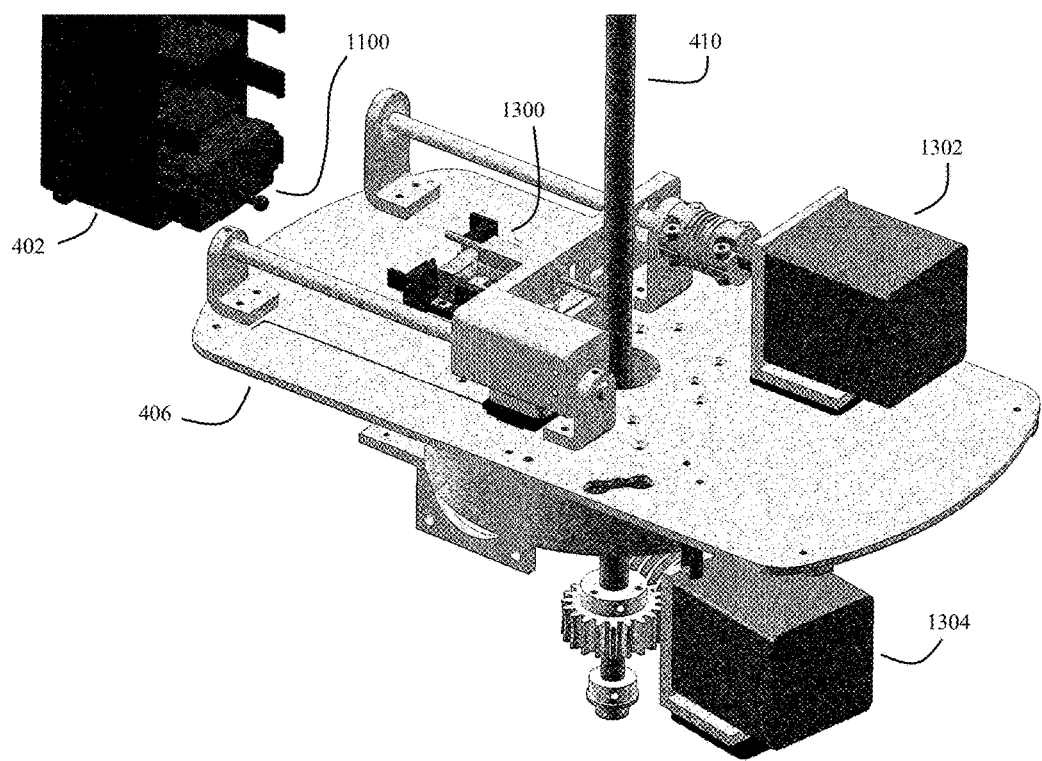
FIG. 13B illustrates a perspective view of how the robotic arm, which pivots around a center point disposed on the axis of a cylinder, can pivot and then move to the appropriate level on a linear cassette. The robotic arm can then use actuator controlled grippers or other devices to then move either the medication itself, or the bin containing the medication, to a drug dispensing location.

FIG. 13B shows another view of this medicine bin grasping process, shown from a different angle, a different arm position, and in solid form. Some of the various processor controlled actuators (electrical motors or other electromechanical actuator device) that may be used by the system are shown as (1302) and (1304).

In some embodiments, also as shown by FIG. 13A and FIG. 13B, the linear cassettes (402) may be configured to hold the second plurality of medicine bins using low force of opening mechanical clasps (1200). Here, for example, the automated medication dispensing device and the linear cassettes (402) may be configured so that automated medication dispensing device can be refilled by removing empty linear cassettes (402), and refilled by inserting medication filled linear cassettes (402). In these embodiments, the low force of opening mechanical clasps (1200) may be configured to retain or hold the medicine bins (1100) in the linear cassettes (402) during storage and transport, but to release the medicine bins (1100) from the linear cassettes (402) upon receiving force (1300) from at least one of the robotic arm's (406) processor controlled actuators (such as 1302).

Figure 14:
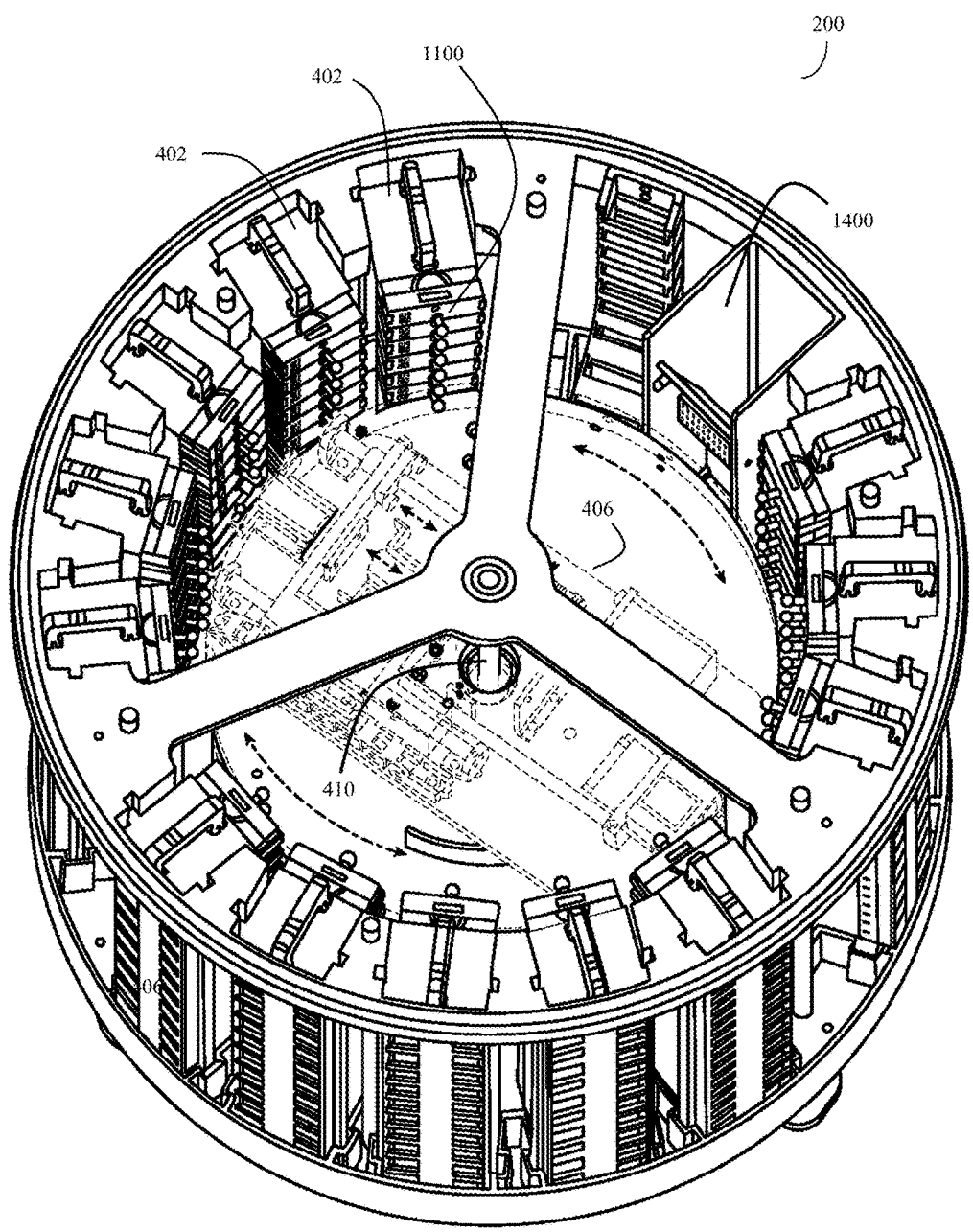
FIG. 14 illustrates a perspective view showing an automated medication dispenser with an ability to hold thirteen (a first plurality) of linear cartridges (twelve are shown loaded). Each linear cartridge holds a second plurality of medicine bins. The rotating robotic arm can swing to the appropriate linear cassette, move to the desired height or location on the cassette, and then select the appropriate medicine bin.

FIG. 14 illustrates a perspective view showing an automated medication dispenser with an ability to hold thirteen (a first plurality) linear cartridges (402) (thirteen are shown loaded), each linear cartridge holding a second plurality of medicine bins (1100). The rotating robotic arm (406) can swing to the appropriate linear cassette (402), move along the axis of the cylinder (410) to the desired height, and select the appropriate medicine bin. The exit pathway (1400) for selected medication bins or medication to then exit to the drug dispensing location is also shown.

In this Figure, the robotic arm (406) is has moved up along the axis (410) to a higher elevation relative to the various linear cassettes (402) so that only the top seven medication bins (1100) can now be see, and the bottom five medication bins are now hidden.

Figure 15:
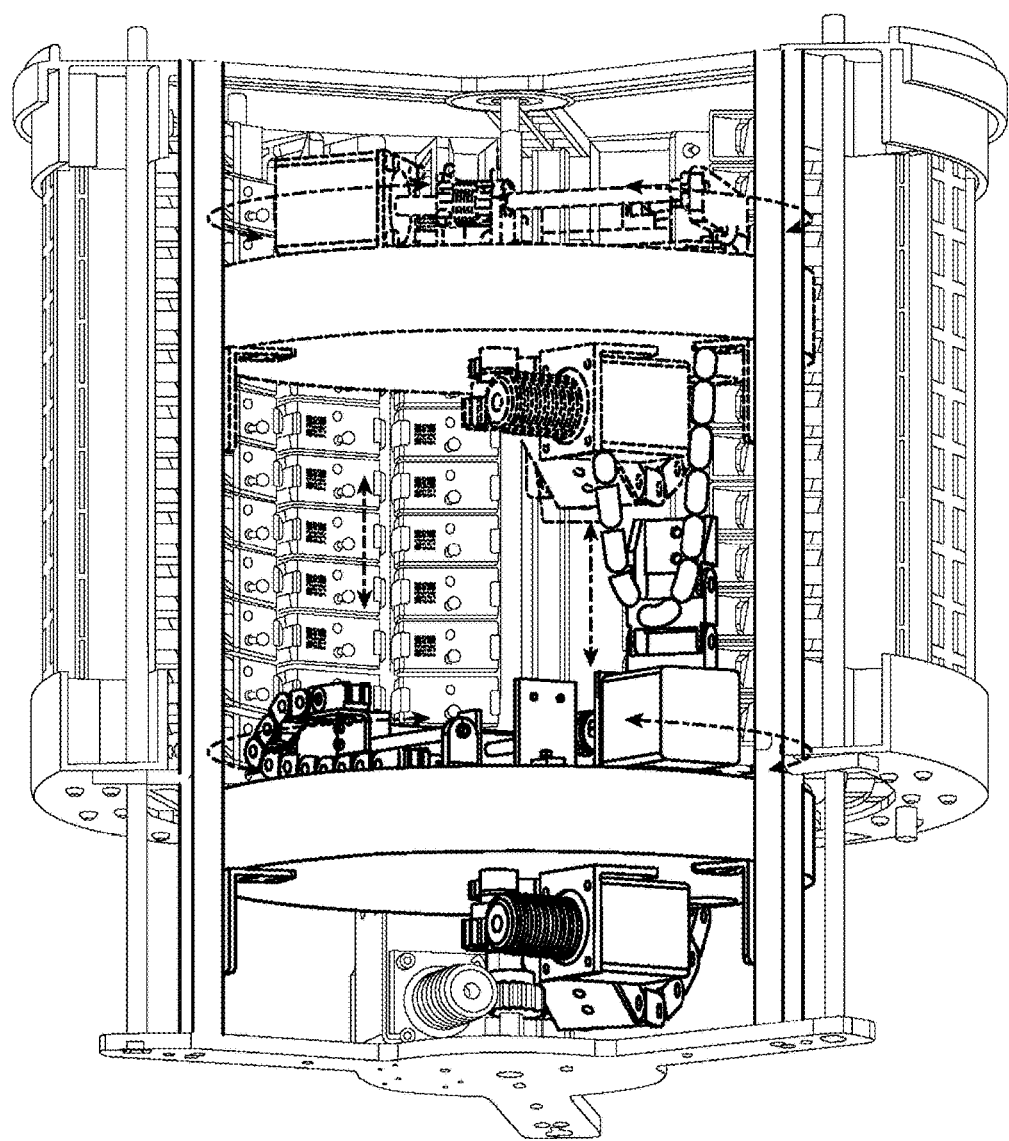
FIG. 15 shows a cross section view of the automated medication device previously shown in FIG. 12, showing the robotic arm moving up and down along the long axis of the linear cassettes, as well as rotating about a center point disposed along the axis of a cylinder.

FIG. 15 shows a cross section view of the device shown in FIG. 14, again showing how the robotic arm (406) has moved up along the axis (410), and thus is now capable of accessing medication bins at a higher elevation or location along the linear cassettes (402). Note that the robotic arm (406) has also rotated along the axis of the cylinder (410) to select a particular processor designated medication bin at a designated location on a designated linear cassette.

Figure 16:
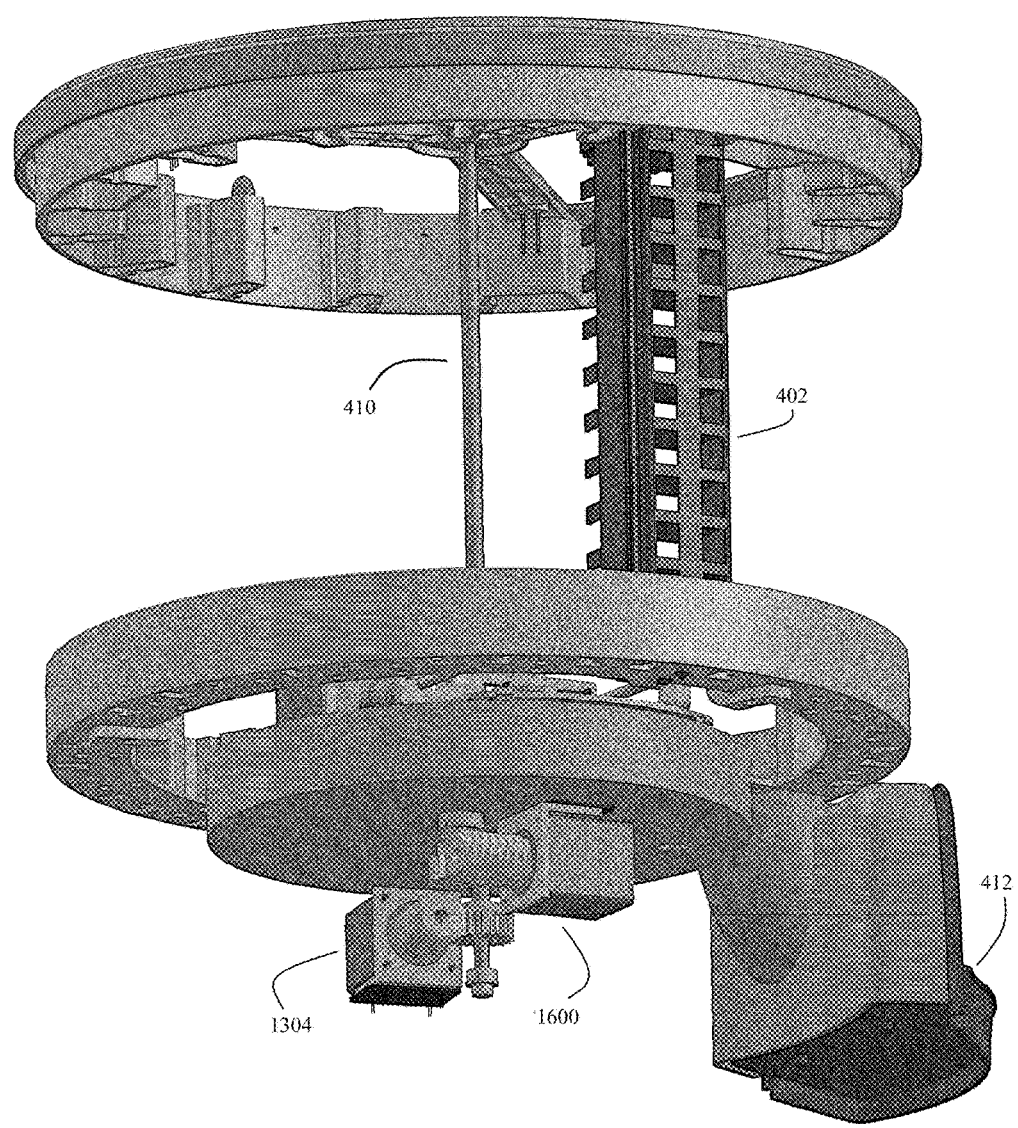
FIG. 16 shows more details of some of the actuators that can control the rotation and movement of the robotic arm.

FIG. 16 shows an alternate view of some of the medication device component, showing an alternate perspective of the linear cassette (402) and drug dispensing location (412), as well as more details of some of the actuators (e.g. 1304) that can control the rotation and movement (up and down the axis 410) of the robotic arm (406).

Figure 17:
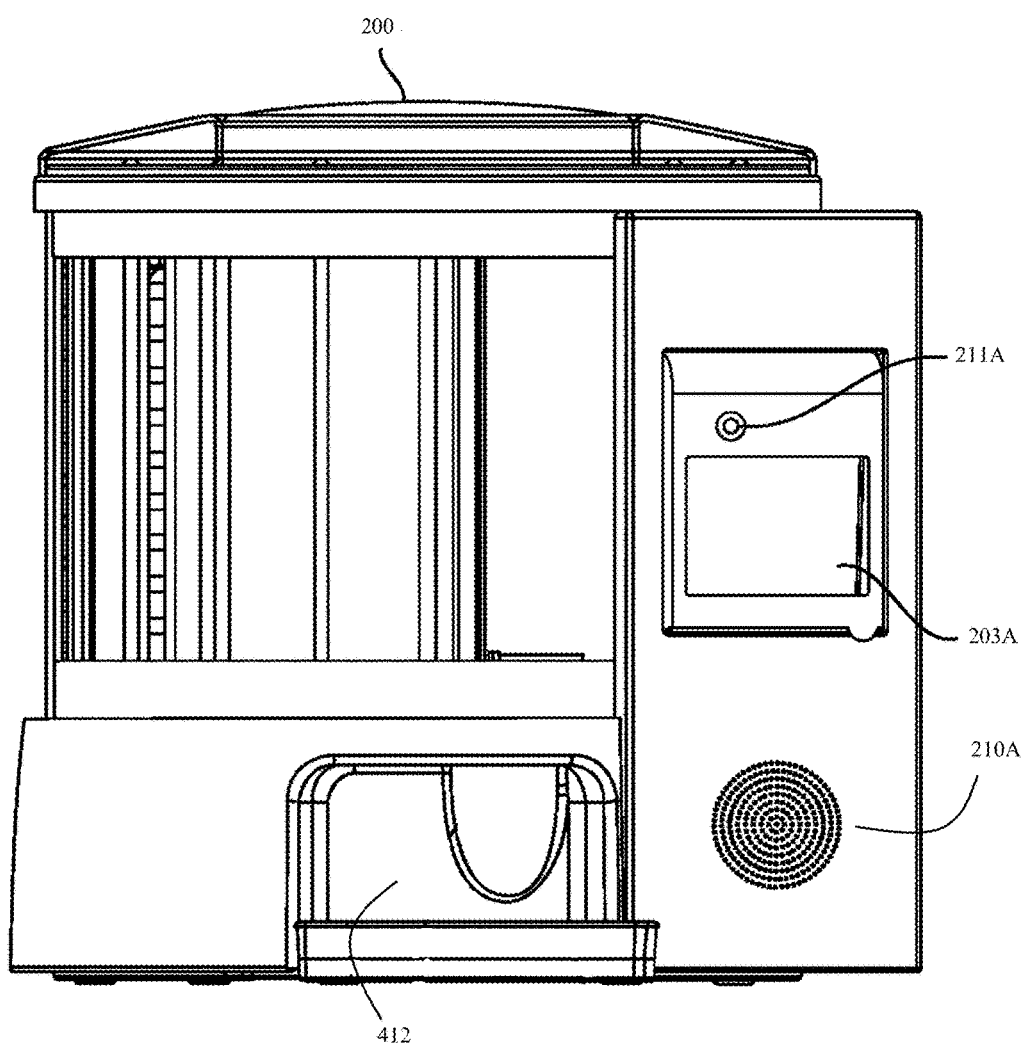
FIG. 17 illustrates an exterior view of a medication dispensing device.

FIG. 17 illustrates an exterior view of a medication dispensing device (200). This also shows various onboard sensors such as a video camera (211A) and microphone (210A), as well as touchscreen user interface (203A).

Figure 18:
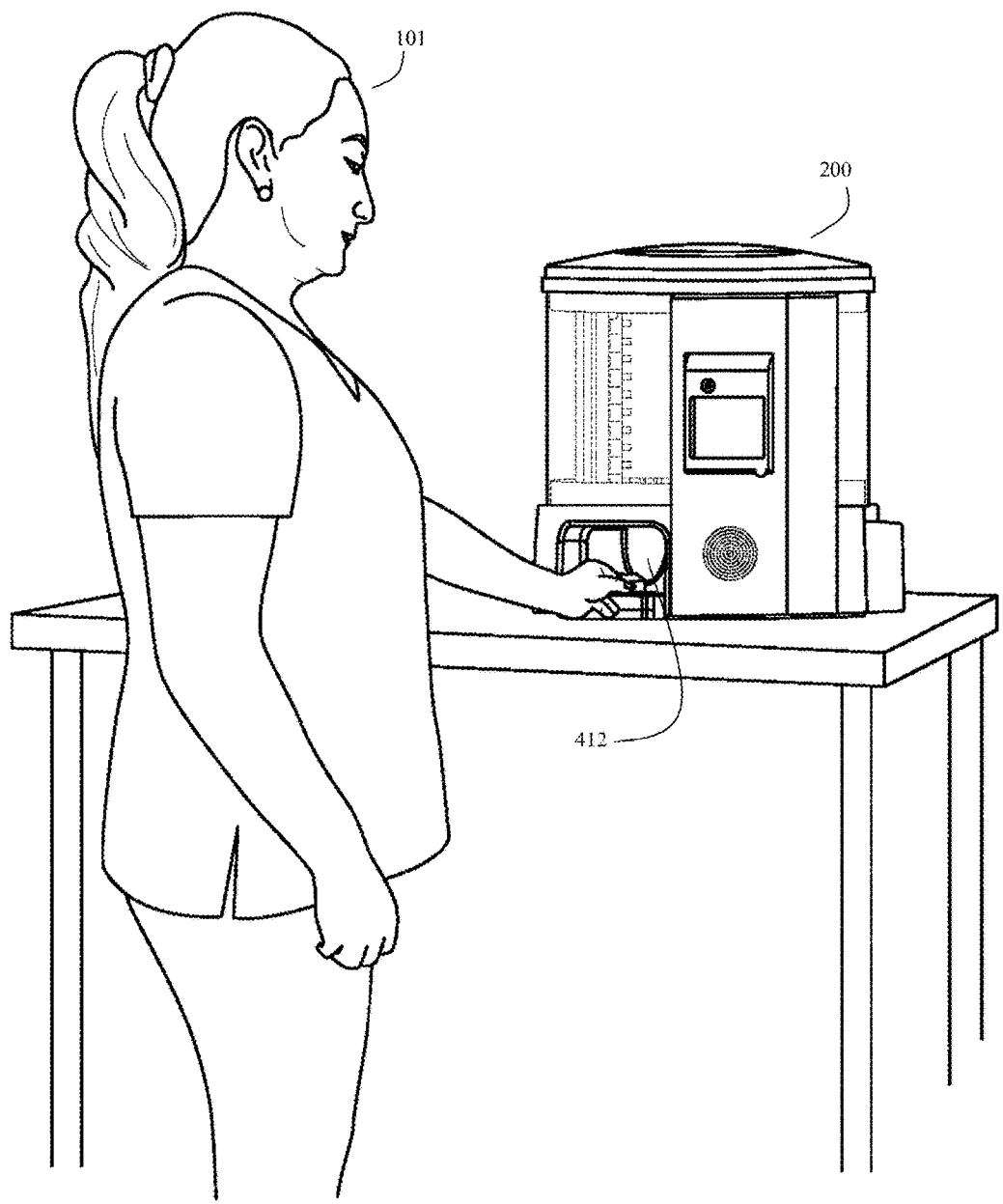
FIG. 18 illustrates an exterior view of a medication dispensing device while in use.

FIG. 18 illustrates an exterior view of a medication dispensing device (200) while in use by a patient (101).

EXAMPLES

Figure 3:
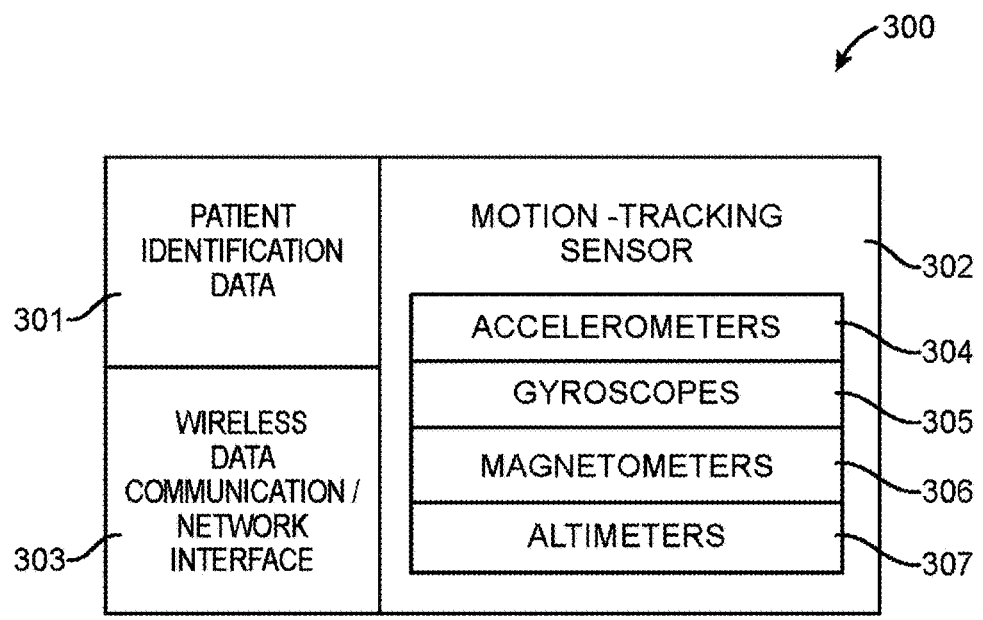
FIG. 3 illustrates a system diagram showing some potential patient worn sensor components, in accordance with an embodiment of the present invention.

An embodiment system of the present invention includes a medication dispensing device 200 communicatively coupled to a medication adherence support device (e.g. remote patient worn sensors) 300. As FIG. 1 illustrates, in some embodiments, the medication adherence support device (remote patient worn sensors) 300 may be embedded in patient worn sensors 102 for use by a patient 101. As FIG. 3 illustrates, in some embodiments, medication adherence support device 300 contains patient identification data 301. In some embodiments medication adherence support device 300 includes one or more of motion-tracking sensors 302. In some embodiments motion tracking sensor 302 comprises: one or more accelerometers 304; one or more gyroscopes 305; one or more magnetometers 306; and one or more altimeters 307. In some embodiments medication adherence support device 300 includes one or more of wireless data communication/network interface 303.

Figure 2:
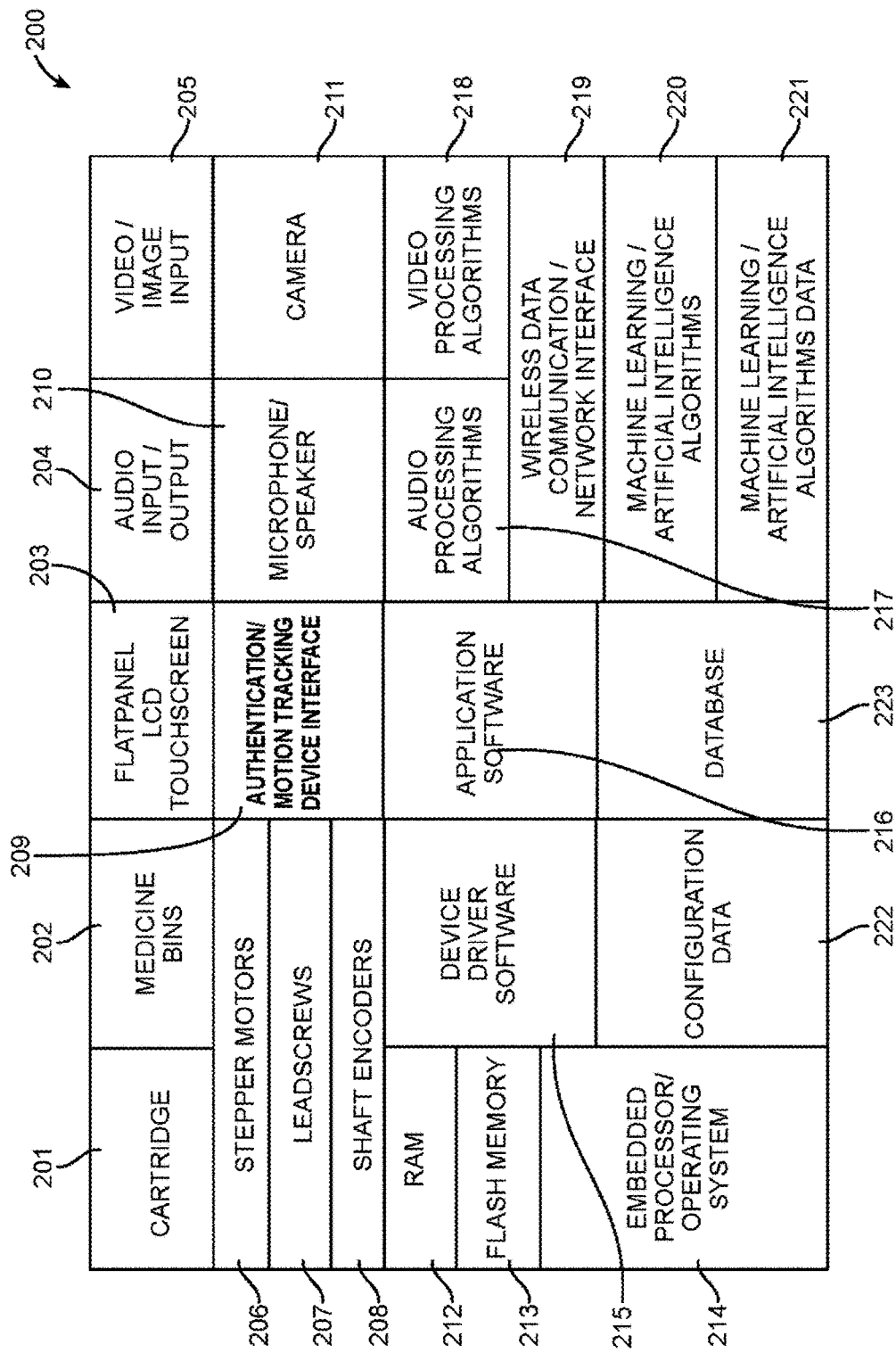
FIG. 2 illustrates a system diagram of the components of a medication dispensing device, in accordance with an embodiment of the present invention.

An overview of some of the various components of present in various embodiments of the invention is shown in block diagram format in FIG. 2. The examples of these various components in a more realistic format are shown in subsequent figures.

Here the medication dispensing device 200 may include a dispensing rack 201 (here, a linear cassette 402 shown elsewhere is a specific type of dispensing rack) and a plurality of medicine bins 202 (a specific type of medicine bin is shown elsewhere as 1100). In some embodiments stepper motors 206 (alternatively referred to elsewhere as actuators such as 1302) and optional lead-screws 207 electro-mechanically operate dispensing rack 201 and medicine bins 202 to dispense medicine doses under control of embedded processor/operating system 214 and application software 216 with the support of device drivers 215.

Device drivers 215 may include stepper motor (a specific type of actuator) control algorithms for operating stepper motors 206. Dispensing rack 201 (e.g. linear cassettes 402), medicine bins 202, stepper motors 206 and lead-screws 207 are configured such that any of medicine bins 202 (e.g. 1100) may be ejected at any time by embedded processor/operating system 214 and application software 216 with the support of device drivers 215 in a random access manner to maximize the variety of dosage opportunities. Other figures such as FIG. 10, FIG. 11, FIG. 12, FIG. 13A, FIG. 13B, FIG. 14, FIG. 15, FIG. 16, FIG. 17, FIG. 18 illustrate the construction and mechanical inter-operation of medicine bins 202 (1100) and dispensing rack 201 (402) to dispense medicine doses under control of embedded processor/operating system 214 and application software 216 with the support of device drivers 215, in accordance with an embodiment of the present invention.

In some embodiments medicine bins 202 and dispensing rack 201 may include magnetic encoders 208 for position sensing and control of the dispensing apparatus. Embedded processor/operating system 214 may execute application software 216 and device drivers 215 from flash memory 213 or RAM 212. In some embodiments a user interface for medication dispensing device 200 may include a flat panel LCD touchscreen 203. In some embodiments medication dispensing device 200 is communicatively coupled with one or more of a medication adherence support device 300 through one or more medication adherence support device interfaces 209. In some embodiments medication adherence support device interface 209 includes one or more of BLE, Wifi, RFID, or NFC. In some embodiments medication dispensing device 200 communicates with a medication adherence support device 300 through medication adherence support device interface 209 to read and authenticate patient identification data 301. In some embodiments medication dispensing device 200 communicates with a medication adherence support device 300 to access real-time motion tracking data from motion tracking sensor 302. In some embodiments motion tracking data from motion tracking sensor 302 comprises: data from one or more accelerometers 304; data from one or more gyroscopes 305; data from one or more magnetometers 306; and data from one or more altimeters 307. In some embodiments medication dispensing device 200 includes audio input/output 204 which may support microphone/speaker 210 for user interface via audio commands or indications. In some embodiments audio input/output 204 and microphone/speaker 210 may provide audio input for one or more audio processing algorithms 217 comprising: voice recognition; speaker identification; and event or activity identification. In some embodiments medication dispensing device 200 includes video/image input 205 which may support camera 211 to provide input to one or more machine vision algorithms 218. In some embodiments machine vision algorithms 218 comprise: motion detection; motion identification; face identification; face detection; gender identification; and, activity identification, including: gesture identification; gait identification; and swallow reflex identification.

Embedded processor/operating system 214, application software 216, and device drivers 215 are configured to authenticate a patient 101 in multiple ways, including, in non-limiting examples: visual authentication, using machine vision algorithms 218 and image or video input from camera 211; audibly, using audio processing algorithms 217, and audio input from microphone/speaker 210; and, cryptographic authentication, using patient identification data 301 in medication adherence support device 300 communicatively (often wirelessly) coupled to medication dispensing device 200 through medication adherence support device interface 209. As disclosed herein, visual authentication of patient 101 identity may be completed using still images such as for face identification, or visual authentication may be completed using moving images such as for gait identification.

Visual or auditory authentication may require a training or configuration stage before authentication for medication adherence is possible. In some embodiments, in a training or configuration stage for visual authentication, a patient's identity may be confirmed by caregivers, and the patient 101 is placed in view of camera 211. For training machine vision algorithms 218 implementing still authentication such as face identification, the patient may be asked to position themselves for adequate training of machine vision algorithms 218. For machine vision algorithms 218 involving moving images, the patient 101 may be asked to perform an exemplary activity, such as walking in view of the camera as in the case of gait identification. One or more machine vision algorithms 218 are configured to train their underlying identification model and presented with image input from camera 211 through video/image input 205 as the patient performs the exemplary activity; the one or more machine vision algorithms 218 complete the training cycle of their underlying identification model, and authentication by machine vision techniques may be performed using the trained algorithms to authenticate the patient.

In some embodiments a training or configuration stage for auditory authentication includes caregivers confirming a patient's identity, and the patient 101 is placed in close proximity to microphone/speaker 210. For training machine audio processing algorithms 217 implementing authentication by speaker identification, the patient may be asked to speak at a certain rate and volume, or may be asked to read a defined passage of text, as an exemplary activity for adequate training of audio processing algorithms 217. One or more audio processing algorithms 217 are configured to train their underlying identification model and presented with audio input from microphone/speaker 210 through audio input/output 204 as the patient speaks; the one or more audio processing algorithms 217 complete the training cycle of their underlying identification model, and authentication by audio processing techniques may be performed using the trained algorithms to authenticate the patient.

In some embodiments a training or configuration stage for confirmation of medication adherence by machine vision motion tracking includes capturing video or a sequence of still images of a patient performing in an exemplary manner the prescribed activity, and presenting the image or video input to machine vision algorithms 218 configured to train their underlying identification model. In a non-limiting example of confirming with machine gesture identification that a patient 101 consumed medication, the patient may be asked to position themselves in view of camera 211 for adequate training of machine vision algorithms 218, and to perform an activity, such as moving their hand from the drug dispensing location in medication dispensing device 200 to grasp in the patient's hand one of medicine bins 202, and then move their hand to the mouth to ingest a medication dose. One or more machine vision algorithms 218 are configured to train their underlying identification model and presented with image input from camera 211 through video/image input 205 as the patient performs the exemplary activity; the one or more machine vision algorithms 218 complete the training cycle of their underlying identification model, and medication adherence by machine vision motion tracking or gesture identification techniques may be performed using the trained algorithms to confirm the patient's gesture such as moving their hand to the mouth, or other activity such as swallowing, was consistent with the exemplary gesture or activity on which the machine vision algorithm was trained.

In some embodiments a training or configuration stage for confirmation of medication adherence by mechanical motion detection includes capturing in medication dispensing device 200 motion-tracking data from motion tracking sensor 302 in patient 101 armband 102 (here armband is simply a particular example) while patient 101 consumes medication from a drug dispensing location in medication dispensing device 200.

In some embodiments, motion tracking data includes: acceleration data from one or more accelerometers 304; angular rotation data from one or more gyroscopes 305, altitude data from one or more altimeters 307, and magnetic field direction and strength data from one or more magnetometers 306. A stream of motion tracking data sampled from motion tracking sensor 302 is provided in real time by motion tracking sensor 302 through medication adherence support device interface 209 to medication dispensing device 200. The motion tracking data from motion tracking sensor 302 includes: time motion started; time motion stopped; acceleration, angular momentum, altitude, and direction and strength of the planetary magnetic field.

As an example of one type of algorithm, the maximum and minimum arc lengths and possible paths that can be traced by a patient's hand when consuming a medication picked up by the patient in the patient's hand and moving the patient's hand to the mouth can be determined from the patient's height. The patient's height can be determined by direct measurement with a measuring tape or stick, or with a machine vision algorithm 218 configured to measure height in combination with, in a non-limiting example, first measuring the patient's distance from the camera which may be accomplished with an ultrasonic proximity detector. The length of a patient's arm from shoulder to wrist and from shoulder to elbow can be estimated from the patient's height. The motion tracking data from motion tracking sensor 302, the patient's height, and estimates or direct measurements of the length of the patient's arm from shoulder to wrist and from shoulder to elbow are used by application software 216 to calculate the limits of a path traced by the patient's hand when consuming medication, and in a training stage, data from an activity or motion exemplary of the prescribed activity is recorded and subsequently used in medication adherence to recognize when a patient 101 has moved their hand consistent with consuming medication dispensed by medication dispensing device 200.

In some embodiments the training stage for medication adherence by the mechanical motion method may include using in addition to acceleration data from one or more accelerometers 304 and angular momentum data from one or more gyroscopes 305, altitude data from one or more altimeters 307 to locate with more accuracy the starting position, or first altitude data, of the patient's hand on the drug dispensing location of medication dispensing device 200. In some embodiments altitude data from one or more altimeters 307 may be used to locate with more accuracy the ending position, or second altitude data, of the patient's hand near or at the patient's mouth, when medication is consumed, and when the patient performs a supervised exemplary activity. In further embodiments the validity of the first altitude data representing the altitude of the patient's hand on the drug dispensing location of medication dispensing device 200 may be enhanced by confirming the patient's hand is in a defined location such as by using an NFC tag or RFID tag in medication adherence support device 300 in combination and in contact with an NFC or RFID scanner in medication dispensing device 200, and using the known relative locations of the drug dispensing location and NFC or RFID scanner to enforce the starting point when a patient is consuming medication.

In still further embodiments, data from one or more magnetometers 306 indicating the direction and strength of the planetary magnetic field may be used to further increase accuracy in tracking the motion of the patient's hand from the drug dispensing location to the patient's mouth, tracking the rotation of the sensor as the patient's hand moves in an arc. When motion tracking data has been recorded from an exemplary medication dose activity, medication adherence by mechanical motion tracking techniques as disclosed herein may be performed by comparing the path traced by the patient's hand when consuming medication by moving their hand to the mouth, was consistent with the exemplary motion data.

In some embodiments, the mechanical motion method of medication adherence, which uses motion tracking data from motion-tracking sensor 302 as disclosed herein, may be used in combination with, or without, medication adherence by other methods such as medication adherence by machine vision motion tracking. In further embodiments, the mechanical motion method of medication adherence, which uses motion tracking data from motion-tracking sensor 302 as disclosed herein, may be used alone, in systems without a camera, as long as the patient's height can be determined. In some embodiments, machine vision motion tracking may be enhanced by using a reflective element on patient worn sensors 102 as a visual target for one or more machine vision algorithms 218. In low light situations or when a patient's arm motion changes due to injury, arthritis, or other medical conditions, machine vision motion tracking may fail, and the mechanical motion method of medication adherence may be used as a backup method in these cases. In addition, the mechanical motion method of medication adherence may be used in combination with machine vision motion tracking methods for medication adherence, using confidence levels obtained from both methods to improve the overall accuracy of medication adherence determinations.

In some embodiments, data from one or more magnetometers 306 indicating the direction and strength of the planetary magnetic field may be used to enable fall detection; a sudden change in the direction of the planetary magnetic field may trigger an alert to caregivers that the patient may have fallen, especially if the change is not soon reversed (a reversal, or approximate return, after a sudden change, to previous magnetometer measurements of direction and strength of the planetary magnetic field, might indicate the patient recovered from their fall).

Figure 5:
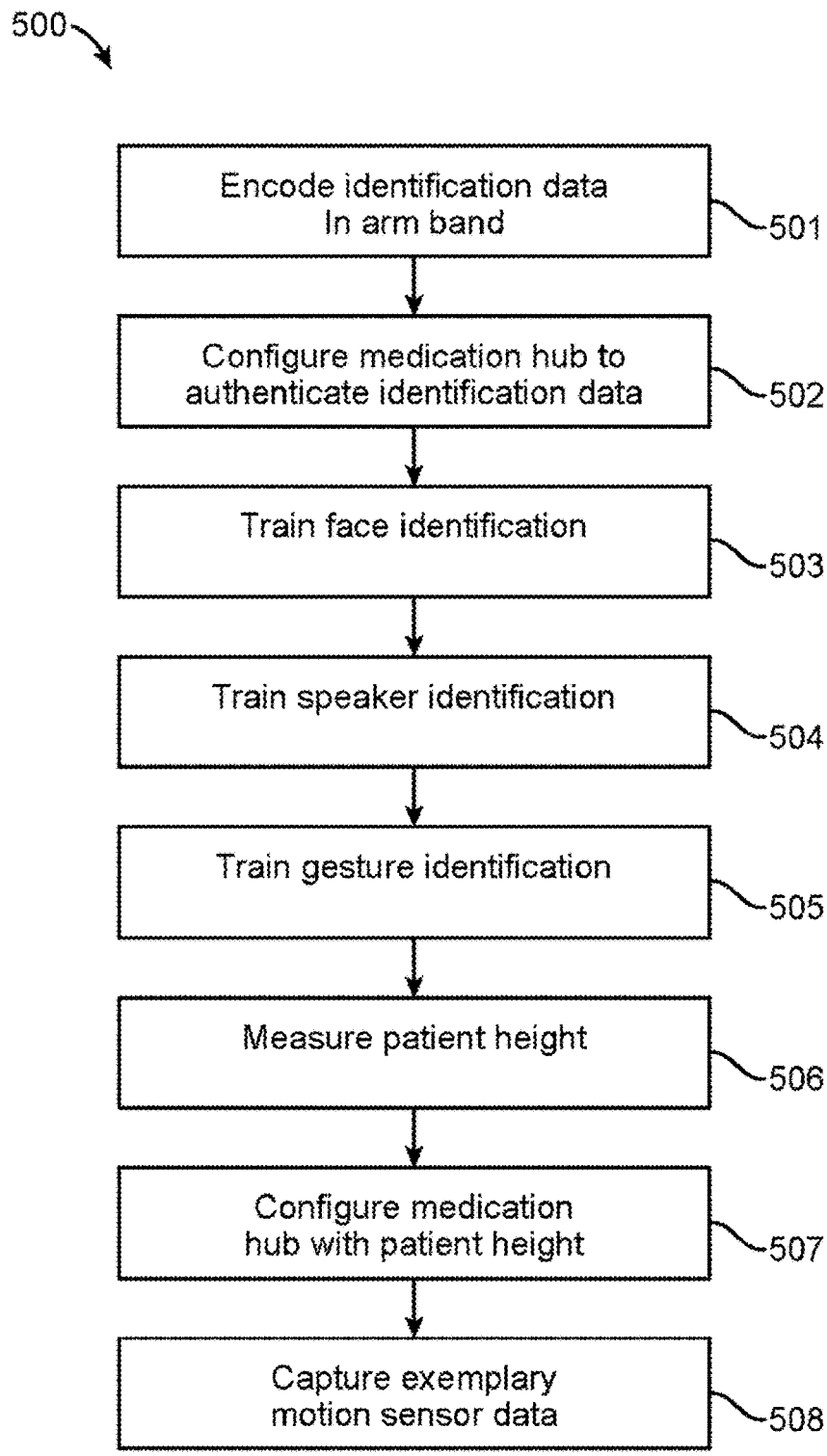
FIG. 5 illustrates a process flow for training and configuration of a medication adherence system, in accordance with an embodiment of the present invention.

Turning now to FIG. 5, in accordance with some embodiments of the present invention, a process flow 500 for training and configuration of a medication adherence system is disclosed. In a first stage, at step 501 patient identification data is encoded in an arm-band containing medication adherence support device 300. In a second stage, at step 502 application software 216 in medication dispensing device 200 is configured to authenticate said patient identification data. In a third stage, at step 503 one or more machine vision algorithms 218 including face identification are trained for patient identification in medication adherence. In a fourth stage, at step 504 one or more machine audio processing algorithms 217 including speaker identification are trained for patient identification in medication adherence. In a fifth stage, at step 505 one or more machine vision algorithms 218 including gesture identification are trained for dose compliance in medication adherence. In a sixth stage, at step 506 one or more patient 101 heights are measured. In a seventh stage, at step 507 application software 216 in medication dispensing device 200 is configured with said one or more patient 101 heights. In an eighth stage, at step 508, exemplary motion sensor data for dose compliance using the mechanical motion tracking method for medication adherence is captured.

Figure 6:
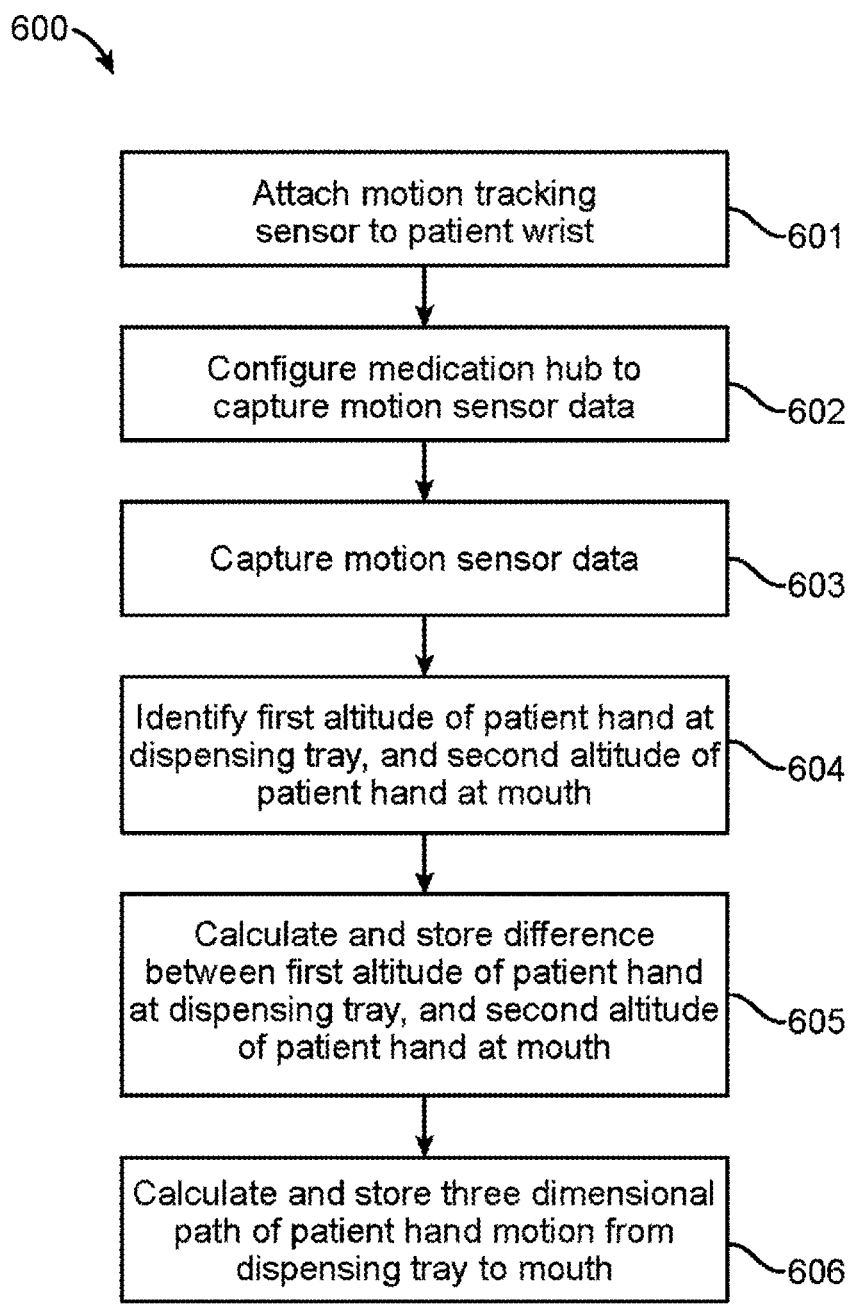
FIG. 6 illustrates a process flow for a method of capturing exemplary data for dose compliance using a mechanical motion tracking method for medication adherence, in accordance with an embodiment of the present invention.

Turning now to FIG. 6, in accordance with some embodiments of the present invention, a process flow 600 for a method of capturing exemplary data for dose compliance using the mechanical motion tracking method for medication adherence is disclosed. In a first stage, at step 601 a motion tracking sensor 302 is attached to wrist of patient 101. In a second stage, at step 602 application software 216 in medication dispensing device 200 is configured to capture data from motion tracking sensor 302 exemplary of patient 101 consuming medication. In a third stage, at step 603 medication dispensing device 200 captures from motion tracking sensor 302 data including: acceleration data from one or more accelerometers 304, angular rotation data from one or more gyroscopes 305, altitude data from one or more altimeters 307, and magnetic field direction and strength data from one or more magnetometers 306, exemplary of patient 101 consuming medication by moving patient 101 hand from the drug dispensing location to mouth of patient 101. In a fourth stage, at step 604, application software 216 in medication dispensing device 200 analyzes said data from motion tracking sensor 302 including altitude data from altimeter 307 to identify: a first altitude of the hand of patient 101 at drug dispensing location, and a second altitude of the hand of patient 101 at the mouth of patient 101. In a fifth stage, at step 605 application software 216 in medication dispensing device 200 calculates and stores for later use the altitude difference between said second altitude and said first altitude of the hand of patient 101 by subtracting said first altitude from said second altitude. In a sixth stage, at step 606 application software 216 in medication dispensing device 200 analyzes said data from motion tracking sensor 302 to calculate and store for later use the three-dimensional path of the hand of patient 101 as medication was consumed, said data from motion tracking sensor 302 including: acceleration data from one or more accelerometers 304, angular rotation data from one or more gyroscopes 305, altitude data from one or more altimeters 307, and magnetic field direction and strength data from one or more magnetometers 306.

Figure 7:
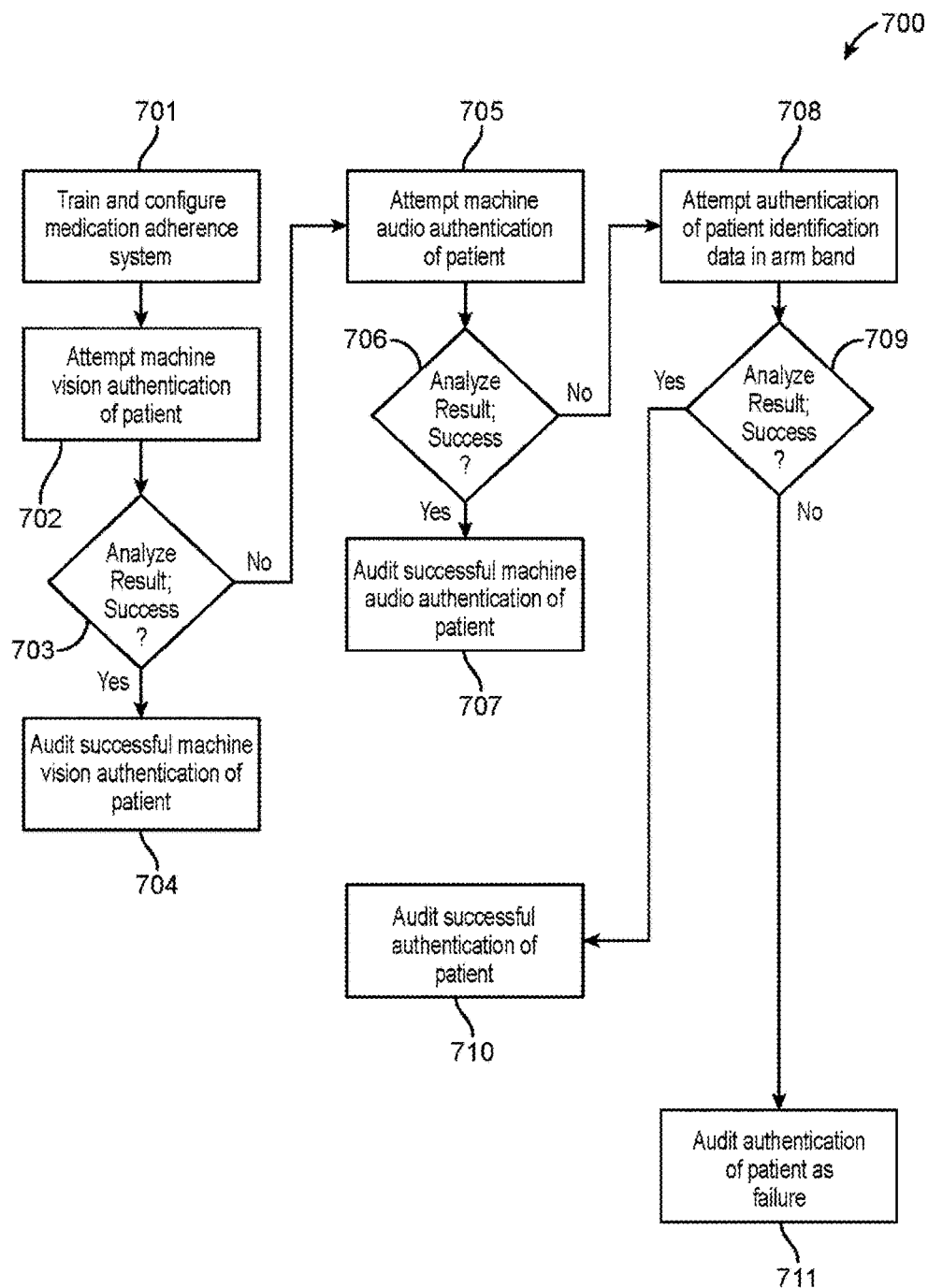
FIG. 7 illustrates a process flow for a method of patient authentication in medication adherence, in accordance with an embodiment of the present invention.

Turning now to FIG. 7, in accordance with some embodiments of the present invention, a process flow 700 for a method of patient 101 authentication in medication adherence is disclosed. In a first stage, at step 701 training and configuration of a medication adherence system is performed as disclosed herein. In a second stage, at step 702 an attempt is made by medication dispensing device 200 to authenticate a patient 101 using one or more machine vision algorithms 218 including face identification. In a third stage, at step 703 one or more results of an attempt to authenticate the patient using one or more machine vision algorithms 218 including face identification are analyzed by application software 216 in medication dispensing device 200 to determine if confidence in said one or more results of an attempt to authenticate the patient 101 using one or more machine vision algorithms 218 including face identification is high. In a fourth stage, at step 704 upon determining confidence in said one or more results of an attempt to authenticate the patient 101 using one or more machine vision algorithms 218 including face identification is high, processing ends with patient 101 authentication audited as successful. In a fifth stage, at step 705 upon determining confidence in said one or more results of an attempt to authenticate patient 101 using one or more machine vision algorithms 218 including face identification is not high, an attempt is made by medication dispensing device 200 to authenticate patient 101 using one or more machine audio processing algorithms 217 including speaker identification. In a sixth stage, at step 706 one or more results of an attempt to authenticate patient 101 using one or more machine audio processing algorithms 217 including speaker identification are analyzed by application software 216 in medication dispensing device 200 to determine if confidence in said one or more results of an attempt to authenticate patient 101 using one or more machine audio processing algorithms 217 including speaker identification is high. In a seventh stage, at step 707 upon determining confidence in said one or more results of an attempt to authenticate patient 101 using one or more machine audio processing algorithms 217 including speaker identification is high, processing ends with patient 101 authentication audited as successful. In an eighth stage, at step 708 upon determining confidence in said one or more results of an attempt to authenticate patient 101 using one or more machine audio processing algorithms 217 including speaker identification is not high, an attempt is made by medication dispensing device 200 to authenticate patient 101 using patient identification data 301 communicatively coupled to medication dispensing device 200. In a ninth stage, at step 709 results of an attempt to authenticate patient 101 using patient identification data 301 communicatively coupled to medication dispensing device 200 are analyzed by application software 216 in medication dispensing device 200 to determine if patient is authenticated. In a tenth stage, at step 710 upon determining patient was authenticated, processing ends with patient 101 authentication audited as successful. In an eleventh stage, at step 711 upon determining patient was not authenticated, processing ends with patient 101 authentication audited as failure.

Figure 8:
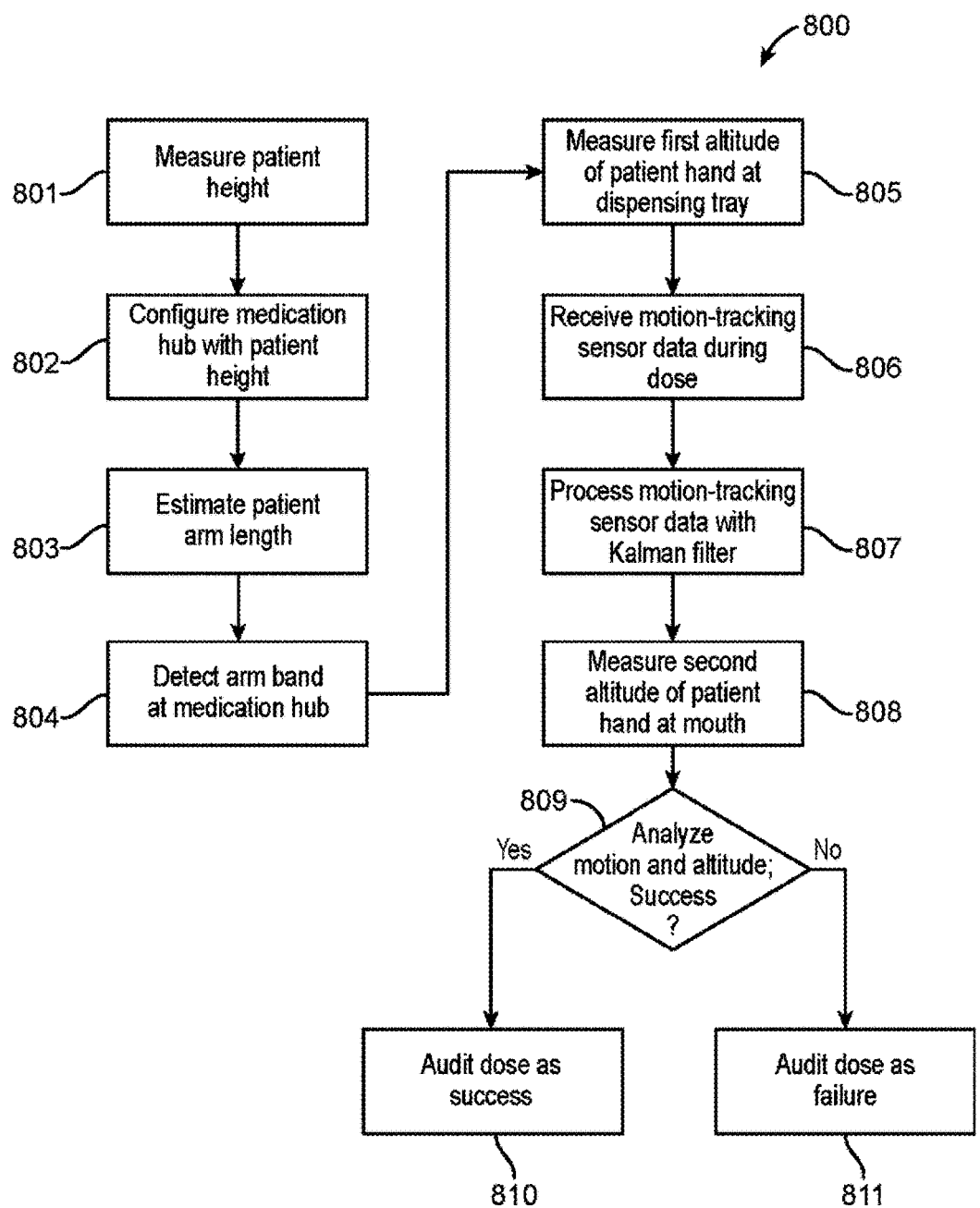
FIG. 8 illustrates a process flow for a motion-tracking method for dose compliance in medication adherence, in accordance with an embodiment of the present invention.

Turning now to FIG. 8, in accordance with some embodiments of the present invention, a process flow 800 for a motion-tracking method for dose compliance in medication adherence is disclosed. In a first stage, at step 801 the height of one or more patient 101 is measured. In a second stage, at step 802 application software 216 is configured with the height of one or more of patient 101. In a third stage, at step 803 application software 216 estimates, using the measured height of a patient 101 and anthropometric data representative of the statistics of human height and arm length, the arm length of patient 101. In a fourth stage, at step 804 medication dispensing device 200 detects, through medication adherence support device interface 209, medication adherence support device 300 attached to wrist of patient 101, in contact with drug dispensing location 412. In a fifth stage, at step 805, application software 216 measures a first altitude of the hand of patient 101 at drug dispensing location 412 using the altitude measured from altimeter 307. In a sixth stage, at step 806 application software 216 receives motion tracking sensor data from medication adherence support device 300 as hand of patient 101 moves from drug dispensing location 402 to mouth of patient 101 to consume medication 1102, 1104, said motion tracking sensor data including: acceleration data from one or more accelerometers 304; angular rotation data from one or more gyroscopes 305, altitude data from one or more altimeters 307, and magnetic field direction and strength data from one or more magnetometers 306. In a seventh stage, at step 807 application software 216 processes said received motion tracking sensor data with one or more of: a low-pass filter, a Kalman filter, or a Complementary filter. In an eighth stage, at step 808, application software 216 measures a second altitude of the hand of patient 101 at the mouth of patient 101 using the altitude measured from altimeter 307. In a ninth stage, at step 809 application software 216 analyzes processed motion tracking sensor data from medication adherence support device 300 to determine if patient hand motion was consistent with a successful dose by one or more of: comparing said processed received motion tracking sensor data to exemplary motion tracking sensor data captured during training and configuration; calculating possible paths for patient hand dosing motion from anthropometric data based on measured height of patient 101 and excluding impossible paths as failed dose attempts; confirming the first altitude is consistent with the altitude of drug dispensing location 412; confirming the second altitude is consistent with the altitude of the mouth of patient 101; and, confirming the difference between said second altitude and said first altitude is consistent with patient 101 having moved their hand from drug dispensing location 412 to the mouth. In n tenth stage, at step 810 upon determining the hand motion of patient 101 was consistent with a successful dose; processing ends with dose compliance audited as success. In an eleventh stage, at step 811 upon determining the hand motion of patient 101 was not consistent with a successful dose, processing ends with dose compliance audited as failure.

Figure 9:
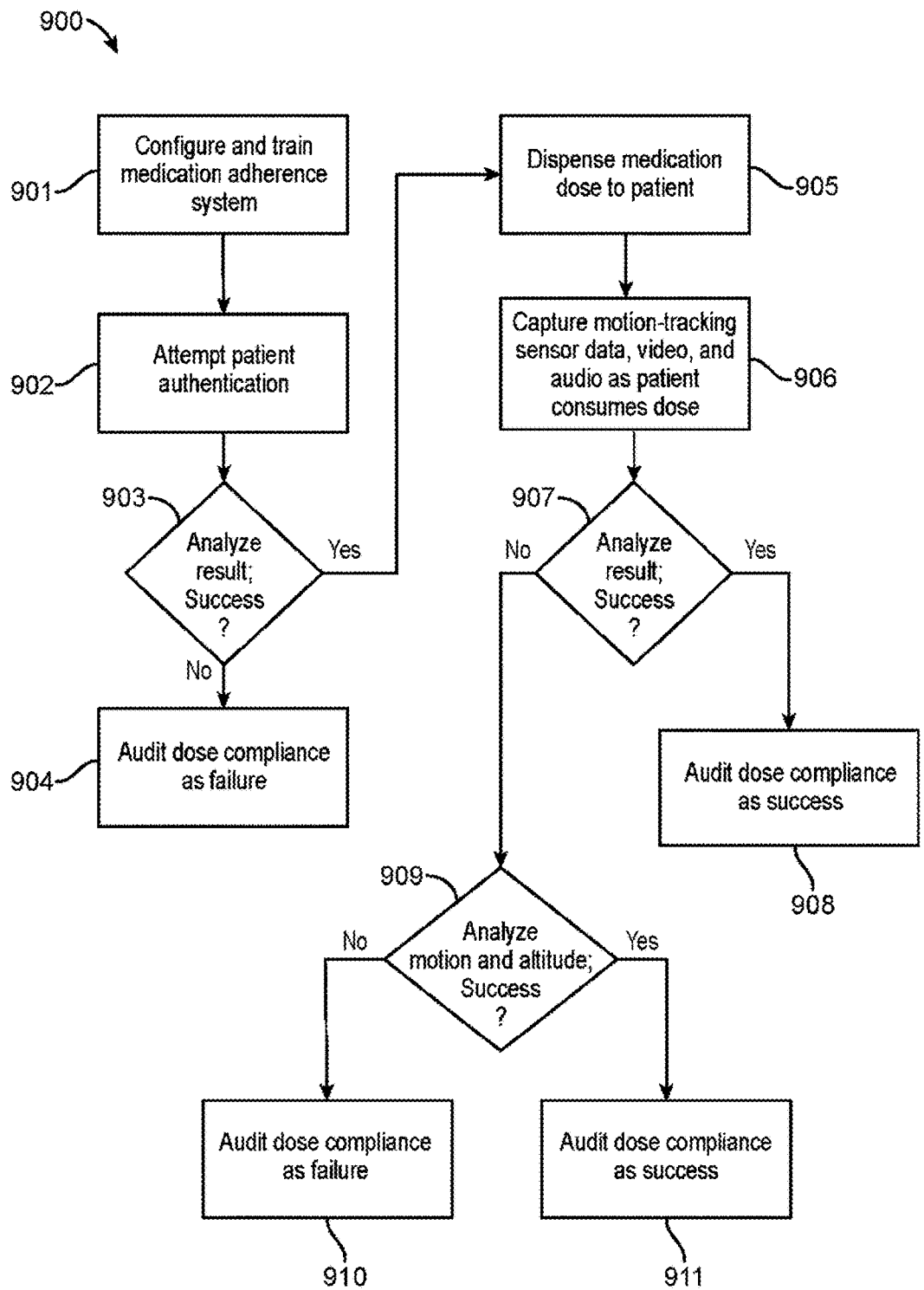
FIG. 9 illustrates a process flow for a method of dose compliance in medication adherence, in accordance with an embodiment of the present invention.

Turning now to FIG. 9, in accordance with some embodiments of the present invention, a process flow 900 for a method of dose compliance in medication adherence is disclosed. In a first stage, at step 901 training and configuration of a medication adherence system comprising medication dispensing device 200 and medication adherence support device 300 is performed as disclosed herein. In a second stage, at step 902, patient authentication for medication adherence is performed by a medication adherence system comprising medication dispensing device 200 and medication adherence support device 300 as disclosed herein. In a third stage, at step 903 the result of patient authentication for medication adherence is analyzed by medication dispensing device 200 to determine if patient authentication for medication adherence succeeded. In a fourth stage, at step 904 upon determining patient authentication for medication adherence did not succeed, processing ends with dose compliance audited as failure. In a fifth stage, at step 905 upon determining patient authentication for medication adherence succeeded, one or more of a medication dose is dispensed by medication dispensing device 200. In a sixth stage, at step 906 medication dispensing device 200 captures observational data representative of activity of patient 101 consuming one or more of a medication dose; said observational data representative of activity of patient 101 including: motion-tracking sensor data from medication adherence support device 300; and video data from one or more camera 211. In a seventh stage, at step 907 video data from one or more of camera 211 representative of activity of patient 101 consuming one or more of a medication dose is analyzed by one or more machine vision algorithms 218 including gesture identification to determine if confidence in patient 101 dose compliance is high. In an eighth stage, at step 908, upon determining confidence in patient 101 dose compliance is high, processing ends with dose compliance audited as success. In a ninth stage, at step 909 upon determining confidence in patient 101 dose compliance is not high, motion-tracking sensor data from medication adherence support device 300 representative of activity of patient 101 consuming one or more of a medication dose is compared, by application software 216 in medication dispensing device 200, with exemplary motion-tracking sensor data collected during training from medication adherence support device 300 to determine if confidence in patient 101 dose compliance is high. In a tenth stage, at step 910, upon determining confidence in patient 101 dose compliance is not high, processing ends with dose compliance audited as failure. In an eleventh stage, at step 911, upon determining confidence in patient 101 dose compliance is high, dose compliance is audited as success.

ADDITIONAL EMBODIMENTS

In some embodiments, the system described herein may additionally use machine/computer vision methods and activity recognition algorithms to further monitor medication compliance.

In these embodiments, the medication adherence device/system may further employ one or more additional sensors, including but not limited to:
1. Time of flight sensors
2. Structured light in conjunction with a video camera such as a CMOS camera 3. Stereo vision (implemented through multiple video cameras)
4. Single video camera (such as a CMOS camera) mounted on the front of the medication adherence system
5. Multiple video cameras (such as multiple CMOS cameras). Here, for example, one video camera may be mounted on the front of the medication adherence system device, and the other may be mounted away from the medication adherence device, such as affixed to the ceiling. Thus, for example, there may be a 90 degree angle between the lines of view of the two cameras.

Here assume that the medication adherence system will work by depositing either a visually distinguishable bin or visually distinguishable pills on the dispensing tray. Assume also that the computer vision system is configured to recognize these bins or pills, such as by colors and shapes (particularly useful for the pills), as well as by visual barcodes (particularly useful for the bins) and the like. So the system effectively will have a priori knowledge of the visual appearance of any bins or pills deposited on the dispensing tray.

Here the system can be configured to track the motion of the patient's face/mouth/hands. The system may additionally be employed to use other automated vision recognition techniques, such as gaze estimation as well. The objective here is to track the trajectory of either the bin or the pills (even if the bin or pills are occluded by the patient's hand or otherwise temporary not visible).

Here, the system's computational task is reduced because there are only a finite (and usually few) number of ways of getting the bin or pills out of the tray, and then (optionally) opening the lid, and ultimately either pouring the pills to the patient's palm or applying the pills directly to the patient's mouth.

In some embodiments, the algorithm can be configured to track that the bin or pills are being held by either the patient's left hand or right hand. As well as optionally the direction of the gaze of the patients eyes when bin or pills are in front of the patient. In some embodiments, when a bin is being used, the bin may have a lid that is constructed in such a way that the lid can be opened with either the same hand that is holding the bin, or the opposite hand.

Continuing with the bin scenario, typically after the lid of the bin has been opened, the contents of the bin can be poured either to the palm of the patient's opposite hand or directly into the patient's mouth.

In those situations where the patient chooses to pour it to the palm of the patient's hand, then the patient can either take the pills from the palm to the mouth, or alternatively use a combination of index/thumb/long fingers to either take all the pills to the mouth or one by one. Typically these different events will be sequential. For example, the system can generally safely assume that the patient's eye gaze direction is not important unless the patient unless the patient actually has the bin or pills in their hand. In a bin with a lid scenario, this may be a time when the patient may need to "solve the problem" of opening the lid of the bin. The system may be configured to either attempt to automatically analyze this using video image recognition algorithms, save a short clip of video from these critical times for later analysis, or record an abstracted version of these events in computer memory for later evaluation.

In some embodiments, when the patient has a set of known and relatively consistent behavioral characteristics, the system may be further configured to use these known and relatively consistent behavioral characteristics to help in its automated scoring process. Consider geriatric patients. These patients tend to repeat certain motion to solve a problem over and over again (that is if they were able to solve it the first time).

In some embodiments, the medication adherence system may be programmed to use on such consistent behavior as part of its alert algorithm. To do this, the system may be configured to either initially, or repeatedly as desired, enter into a "learning mode" for a period of time, such as a week. During such learning modes, the system can be configured to attempt to determine such consistent behaviors.

For example, the system may be programmed with one or more algorithms that put the system into a learning mode when initially started up. Here the system might observe the patient's behavior, possibly using machine learning methods, and determine the patients behavioral characteristics, but possibly not warn the caregiver about potential problems because the system is still in training. After a period of time, such as a week, the system can then be configured to run in "production mode". In "production mode", typically the system will be configured to alert the caregivers if the patient deviates from his/her traditional patterns. Various types of alerts are possible. Some alerts may not mean that that the patient has not complied with their medication regimen, it may simply mean that the patient has deviated from previous behavioral patterns, and thus may not have taken the medication. Other alerts, such as a complete absence of any patient activity during critical mediation times, can be scored as probable deviation from medication adherence. These alerts may be stored in computer memory for later retrieval, or alternatively a caretaker may be immediately summoned, depending on the system settings.

As desired, the patient's caregiver can choose to download the relevant patient behavior computer files, and as desired audit the various interactions. The caregiver may even, for example, play back audio or video records of the relevant alerts, and thus effectively use the system to help revert back to traditional "Directly observable therapy" (DOT). The caregiver can then decide to, as necessary override the system's scoring of the event (e.g. review video, and correct the system's automated evaluation of the data).

In some embodiments, the system can also be configured to automatically recognize aberrant events, such as cases when the patient drops pills on the floor, and send automatic alerts to caregivers as desired. Such aberrant events are, unfortunately, a significant problem with Alzheimer/Parkinson patients, and thus an ability to cope with these situations can be desirable.

The invention claimed is:

1. A method of operating an automated medication dispensing device, said method comprising:
providing an automated medication dispensing device;
said automated medication dispensing device configured to store a plurality of different medications in a plurality of individual robotically removable medicine bins, each medicine bin storing a unit dose of at least one medication;
wherein said automated medication dispensing device further comprises a processor, communications interface, onboard sensors, and at least one processor controlled electronic actuator;
wherein said automated medication dispensing device automatically dispenses said at least one medication by using said at least one processor controlled actuator to rotate around an axis of a cylinder or partial cylinder and automatically retrieve an appropriate medicine bin containing said at least one medication from a storage position disposed along a circumference of said cylinder or partial cylinder, and to deliver said medicine bin to at least one patient;

receiving medication dispensing information, said medication dispensing information comprising medication timing information and medication patient assignment information;

using said onboard sensors and reference patient identity information to determine an identity of at least one patient;

using said patient identity information, said medication dispensing information, and time information to automatically dispense said at least one medication for said at least one patient;

using any of said onboard sensors or information obtained from remote patient worn sensors to obtain evidence that said patient is being properly medicated;

and storing or transmitting a record pertaining to said evidence.

2. The method of claim 1, wherein said automated medication dispensing device further comprises a user interface, and any of said medication dispensing information or reference patient identity information is entered using said user interface.

3. The method of claim 1, wherein said onboard sensors comprise any of video or time-of-flight or audio sensors, and said automated medication dispensing device uses automated video or time-of-flight or audio analysis software to confirm said identity of at least one patient.

4. The method of claim 1, wherein said patient wears a radiofrequency identification tag or other identification device, said onboard sensors comprise radiofrequency identification tag or other identification device sensors, and said onboard sensors use information obtained from said radiofrequency identification tag or other identification device to confirm said identity of at least one patient.

5. The method of claim 1, wherein said onboard sensors comprise any of video or audio sensors, and said automated dispensing device uses automated video or audio analysis software to obtain evidence that said patient has taken said medication.

6. The method of claim 1, wherein remote patient worn sensors comprise patient worn motion or position sensors with wireless connectivity to said automated medication dispensing device;

wherein said automated medication dispensing device uses patient motion or position data obtained from said patient worn motion or position sensors to obtain evidence that said patient is being properly medicated.

7. The method of claim 6, wherein said patient worn motion or position sensors are worn on an arm or wrist of said patient.

8. The method of claim 6, wherein said patient worn motion sensors further report on a motion or position status of the patient on a continuing basis; and wherein said automated medication dispensing device uses evidence of abnormal patient motion or position as evidence that said patient is not being properly medicated.

9. The method of claim 8, wherein said evidence comprises evidence of patient lack of motion, tremors, or patient position outside of predetermined position limits.

10. The method of claim 1, wherein said medicine bins are configured to hold unit doses of a plurality of different medications;

said medicine bin further comprises a protruding handle; and said processor controlled actuator is further configured grasp said protruding handle.

11. The method of claim 1, wherein each medicine bin is configured to store a unit dose of at least one medication, and said plurality of medicine bins are distributed into a plurality of removable linear cassettes, each removable linear cassette storing a plurality of medicine bins;

said plurality of removable linear cassettes disposed in a cylindrical or partial cylindrical wall manner around a robotic arm that pivots around a center point disposed along said axis of said cylinder, said removable linear cassettes positioned with their longest dimension parallel to said axis;

wherein said processor controlled actuators direct said robotic arm to rotate around said axis to a processor designated linear cassette, move along said axis to a specific level on said linear cassette where a designated medicine bin is located, retrieve said designated medicine bin and automatically dispense medication by depositing said medicine bin in a drug dispensing location of said automated medication dispensing device.

12. The method of claim 11, wherein said linear cassettes are configured to hold said plurality of medicine bins using low force of opening mechanical clasps;

said automated medication dispensing device and said linear cassettes configured so that said automated medication dispensing device can be refilled by removing empty linear cassettes, and refilled by inserting medication filled medicine bins into said linear cassettes producing filled linear cassettes, and then reinserting said filled linear cassettes;

said low force of opening mechanical clasps configured to retain said medicine bins in said linear cassettes during storage and transport, but to release said medicine bins from said linear cassettes upon receiving force from at least one of said robotic arm's processor controlled actuators.

13. The method of claim 1, wherein said automated medication dispensing device uses said communications interface to receive patient identity information from a remote computerized device.

14. An automated medication dispensing device, said device comprising a processor, communications interface, onboard sensors, and at least one processor controlled electronic actuator;

said automated medication dispensing device configured to store a plurality of different medications in a plurality of individual robotically removable medicine bins, each storing a unit dose of at least one medication;

said at least one processor configured with software stored in non-transient memory to direct said processor send commands to said at least one processor controlled actuator to rotate around an axis of a cylinder or partial cylinder and automatically dispense medication by automatically retrieving, from a storage position disposed along a circumference of said cylinder or partial cylinder, an appropriate medicine bin containing said at least one medication, and to deliver said medicine bin to a medication access port that is accessible by at least one patient;

said software and processor further configured to receive medication dispensing information comprising medication timing information and medication patient assignment information, and to use said onboard sensors and reference patient identity information to determine an identity of at least one patient;

said software and processor further configured to use said patient identity information, said medication dispensing information, and time information to automatically dispense medication for said at least one patient;

said software and processor further configured to use any of said onboard sensors or information obtained from remote patient worn sensors to obtain evidence that said patient is being properly medicated; and said software and processor further configured to and store or transmit a record pertaining to said evidence.

15. The device of claim 14, wherein each medicine bin is configured to store a unit dose of medication, said plurality of medicine bins distributed into a plurality of removable linear cassettes, each removable linear cassette storing a plurality of medicine bins;

said plurality of removable linear cassettes disposed in a cylindrical or partial cylindrical circumference manner around a robotic arm that pivots around a center point disposed along said axis of said cylinder, said removable linear cassettes positioned with their longest dimension parallel to said axis;

wherein said software and processor controlled actuators are configured to direct said robotic arm to rotate around said axis to a processor designated linear cassette, move along said axis to a specific level on said linear cassette where a designated medicine bin is located, and retrieve said designated medicine bin and automatically dispense medication by depositing said medicine bin in a drug dispensing location of said automated medication dispensing device.

16. The device of claim 15, wherein said linear cassettes are configured to hold said plurality of medicine bins using low force of opening mechanical clasps;

said automated medication dispensing device and said linear cassettes configured so that said automated medication dispensing device can be refilled by removing empty linear cassettes, and refilled by inserting medication filled medicine bins into said linear cassettes producing filled linear cassettes, and then reinserting said filled linear cassettes;

said low force of opening mechanical clasps configured to retain said medicine bins in said linear cassettes during storage and transport, but to release said medicine bins from said linear cassettes upon receiving force from at least one of said robotic arm's processor controlled actuators.

* * * * *